US012575817B2

(12) United States Patent
Walen et al.

(10) Patent No.: US 12,575,817 B2
(45) Date of Patent: *Mar. 17, 2026

(54) SYSTEMS AND METHODS OF PERFORMING SPINE SURGERY AND MAINTAINING A VOLUME OF FLUID AT A SURGICAL SITE

(71) Applicant: Stryker Corporation, Portage, MI (US)

(72) Inventors: James G. Walen, Portage, MI (US); Steven J. Carusillo, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 24 days.

This patent is subject to a terminal disclaimer.

(21) Appl. No.: 18/816,411

(22) Filed: Aug. 27, 2024

(65) Prior Publication Data

US 2024/0415503 A1 Dec. 19, 2024

Related U.S. Application Data

(63) Continuation of application No. 17/287,565, filed as application No. PCT/US2019/057599 on Oct. 23, 2019, now Pat. No. 12,114,846.

(Continued)

(51) Int. Cl.
*A61B 17/02* (2006.01)
*A61B 17/00* (2006.01)
(Continued)

(52) U.S. Cl.
CPC ........ *A61B 17/0218* (2013.01); *A61B 17/025* (2013.01); *A61B 90/06* (2016.02);
(Continued)

(58) Field of Classification Search
CPC ...... A61B 2562/0247; A61B 2217/005; A61B 2017/0256; A61B 2017/00261;
(Continued)

(56) References Cited

U.S. PATENT DOCUMENTS 4,650,462 A * 3/1987 DeSatnick .......... A61M 3/0216
601/2
5,131,382 A 7/1992 Meyer
(Continued)

FOREIGN PATENT DOCUMENTS

EP 1880686 A2 1/2008
EP 1781353 B1 7/2013
(Continued)

OTHER PUBLICATIONS

English language abstract for JP 2007-522837 A extracted from espacenet.com database on Jul. 21, 2023, 1 page.
(Continued)

*Primary Examiner* — Kevin T Truong
*Assistant Examiner* — Diana Jones
(74) *Attorney, Agent, or Firm* — Howard & Howard Attorneys PLLC

(57) ABSTRACT

Systems and methods for performing spine surgery. A retractor may be positioned within a patient to facilitate maintaining a volume of fluid at the surgical site. The retractor includes an opening capable of receiving one or more surgical instruments, for example, a cutting instrument and an endoscope. A cutting member of the cutting instrument is submerged and operated within the volume of fluid to resect tissue, for example, within the intervertebral disc space. The volume of fluid is maintained at the surgical site improves cooling of the surgical site and visualization of the surgical site via the endoscope during resection. The volume of fluid is maintained at the surgical site via the surgical system. The surgical system may include a sensor for measuring the level of fluid in the retractor, an inflow source and an outflow source in fluid communication with the retractor, and a controller controlling the surgical system.

20 Claims, 13 Drawing Sheets

Related U.S. Application Data

(60) Provisional application No. 62/751,964, filed on Oct. 29, 2018.

(51) Int. Cl.
    *A61B 90/00*     (2016.01)
    *A61M 1/00*     (2006.01)

(52) U.S. Cl.
    CPC ............... *A61B 2017/00026* (2013.01); *A61B 2017/00261* (2013.01); *A61B 2017/0256* (2013.01); *A61B 2217/005* (2013.01); *A61B 2217/007* (2013.01); *A61B 2562/0247* (2013.01); *A61M 1/77* (2021.05)

(58) Field of Classification Search
    CPC ........ A61B 2017/00026; A61B 17/025; A61B 90/06; A61B 17/0218; A61M 1/77
    See application file for complete search history.

(56) References Cited

U.S. PATENT DOCUMENTS

| | | | |
|---|---|---|---|
| 5,439,464 A | 8/1995 | Shapiro | |
| 5,472,426 A | 12/1995 | Bonati et al. | |
| 5,543,695 A | 8/1996 | Culp et al. | |
| 5,635,777 A | 6/1997 | Telymonde et al. | |
| 5,643,203 A | 7/1997 | Beiser et al. | |
| 5,654,203 A * | 8/1997 | Ohtani .............. H01L 21/02686 | |
| | | | 438/162 |
| 5,689,159 A | 11/1997 | Culp et al. | |
| 5,787,760 A | 8/1998 | Thorlakson | |
| 5,800,383 A | 9/1998 | Chandler et al. | |
| 5,865,832 A | 2/1999 | Knopp et al. | |
| 5,983,749 A | 11/1999 | Holtorf | |
| 6,017,354 A | 1/2000 | Culp et al. | |
| 6,090,123 A | 7/2000 | Culp et al. | |
| 6,099,522 A | 8/2000 | Knopp et al. | |
| 6,150,623 A | 11/2000 | Chen | |
| 6,152,941 A | 11/2000 | Himes et al. | |
| 6,260,434 B1 | 7/2001 | Holtorf | |
| 6,287,304 B1 | 9/2001 | Eggers et al. | |
| 6,329,778 B1 | 12/2001 | Culp et al. | |
| 6,360,630 B2 | 3/2002 | Holtorf | |
| 6,371,121 B1 | 4/2002 | Faries, Jr. et al. | |
| 6,452,120 B1 | 9/2002 | Chen | |
| 6,452,123 B1 | 9/2002 | Chen | |
| 6,475,215 B1 | 11/2002 | Tanrisever | |
| 6,689,146 B1 | 2/2004 | Himes | |
| 6,702,809 B1 | 3/2004 | Knopp et al. | |
| 6,726,680 B1 | 4/2004 | Knopp et al. | |
| 6,741,948 B2 | 5/2004 | Hauger et al. | |
| 6,752,816 B2 | 6/2004 | Culp et al. | |
| 6,780,184 B2 | 8/2004 | Tanrisever | |
| 6,860,271 B2 | 3/2005 | Faries, Jr. et al. | |
| 6,893,261 B1 | 5/2005 | Feine | |
| 6,913,603 B2 | 7/2005 | Knopp et al. | |
| 6,918,395 B2 | 7/2005 | Faries, Jr. et al. | |
| 7,238,010 B2 | 7/2007 | Hershberger et al. | |
| 7,247,161 B2 | 7/2007 | Johnston et al. | |
| 7,259,340 B2 | 8/2007 | Blaha et al. | |
| 7,276,059 B2 | 10/2007 | Irwin | |
| 7,318,831 B2 | 1/2008 | Alvarez et al. | |
| 7,353,068 B2 | 4/2008 | Tanaka et al. | |
| 7,416,539 B2 | 8/2008 | Johnston et al. | |
| 7,422,432 B2 | 9/2008 | Warner | |
| 7,422,582 B2 | 9/2008 | Malackowski et al. | |
| 7,439,463 B2 | 10/2008 | Brenner et al. | |
| 7,462,187 B2 | 12/2008 | Johnston et al. | |
| 7,473,263 B2 | 1/2009 | Johnston et al. | |
| 7,485,116 B2 | 2/2009 | Cao | |
| 7,488,285 B2 | 2/2009 | Honda et al. | |
| 7,517,351 B2 | 4/2009 | Culp et al. | |
| 7,557,317 B2 | 7/2009 | Blaha et al. | |
| 7,608,039 B1 | 10/2009 | Todd | |
| 7,619,171 B2 | 11/2009 | Horvath et al. | |
| 7,621,898 B2 | 11/2009 | Lalomia et al. | |
| 7,625,208 B2 | 12/2009 | Warner | |
| 7,636,549 B2 | 12/2009 | Ma et al. | |
| 7,717,931 B2 | 5/2010 | Himes | |
| 7,731,677 B2 | 6/2010 | Sakurai | |
| 7,781,941 B2 | 8/2010 | Horvath et al. | |
| 7,799,044 B2 | 9/2010 | Johnston et al. | |
| 7,886,749 B2 | 2/2011 | Irwin | |
| 7,998,157 B2 | 8/2011 | Culp et al. | |
| 8,120,301 B2 | 2/2012 | Goldberg et al. | |
| 8,159,370 B2 | 4/2012 | Shields et al. | |
| 8,175,590 B2 | 5/2012 | Hamel et al. | |
| 8,216,199 B2 | 7/2012 | Murray et al. | |
| 8,274,376 B2 | 9/2012 | Shields et al. | |
| 8,292,879 B2 | 10/2012 | Manwaring et al. | |
| 8,337,097 B2 | 12/2012 | Cao | |
| 8,372,066 B2 | 2/2013 | Manwaring et al. | |
| 8,377,052 B2 | 2/2013 | Manwaring et al. | |
| 8,380,126 B1 | 2/2013 | Ma et al. | |
| 8,414,569 B2 | 4/2013 | Manwaring et al. | |
| 8,419,724 B2 | 4/2013 | Manwaring et al. | |
| 8,425,503 B2 | 4/2013 | Manwaring et al. | |
| 8,430,870 B2 | 4/2013 | Manwaring et al. | |
| 8,454,640 B2 | 6/2013 | Johnston et al. | |
| 8,465,473 B2 | 6/2013 | Horvath | |
| 8,475,481 B2 | 7/2013 | Himes | |
| 8,486,056 B2 | 7/2013 | Irwin | |
| 8,491,578 B2 | 7/2013 | Manwaring et al. | |
| 8,506,561 B2 | 8/2013 | Manwaring et al. | |
| 8,508,173 B2 | 8/2013 | Goldberg et al. | |
| 8,523,850 B2 | 9/2013 | Manwaring et al. | |
| 8,523,851 B2 | 9/2013 | Manwaring et al. | |
| 8,523,852 B2 | 9/2013 | Manwaring et al. | |
| 8,537,210 B2 | 9/2013 | Omori et al. | |
| 8,551,088 B2 | 10/2013 | Falkenstein et al. | |
| 8,562,598 B2 | 10/2013 | Falkenstein et al. | |
| 8,565,839 B2 | 10/2013 | Ma et al. | |
| 8,568,411 B2 | 10/2013 | Falkenstein et al. | |
| 8,579,894 B2 | 11/2013 | Falkenstein et al. | |
| 8,638,056 B2 | 1/2014 | Goldberg et al. | |
| 8,638,057 B2 | 1/2014 | Goldberg et al. | |
| 8,641,609 B2 | 2/2014 | Hestad et al. | |
| 8,653,919 B2 | 2/2014 | Culp et al. | |
| 8,657,809 B2 | 2/2014 | Schoepp | |
| 8,680,412 B2 | 3/2014 | Horvath et al. | |
| 8,725,096 B2 | 5/2014 | Lint et al. | |
| 8,740,866 B2 | 6/2014 | Reasoner et al. | |
| 8,749,188 B2 | 6/2014 | Tran et al. | |
| 8,750,796 B2 | 6/2014 | Claus et al. | |
| 8,768,251 B2 | 7/2014 | Claus et al. | |
| 8,834,457 B2 | 9/2014 | Cao | |
| 8,915,897 B2 | 12/2014 | Murray et al. | |
| 8,915,910 B2 | 12/2014 | Falkenstein et al. | |
| 8,923,768 B2 | 12/2014 | Ma et al. | |
| 8,937,561 B2 | 1/2015 | Shields et al. | |
| 8,961,040 B2 | 2/2015 | Cao | |
| 8,967,883 B2 | 3/2015 | Cao | |
| 9,078,655 B2 | 7/2015 | Manwaring et al. | |
| 9,107,666 B2 | 8/2015 | Manwaring et al. | |
| 9,131,034 B2 | 9/2015 | Ma et al. | |
| 9,131,977 B2 | 9/2015 | Manwaring et al. | |
| 9,149,238 B2 | 10/2015 | Watkins | |
| 9,162,078 B2 | 10/2015 | Irwin | |
| 9,168,091 B2 | 10/2015 | Janssen et al. | |
| 9,220,557 B2 | 12/2015 | Manwaring et al. | |
| 9,233,193 B2 | 1/2016 | Truckai et al. | |
| 9,265,553 B2 | 2/2016 | Manwaring et al. | |
| 9,265,554 B2 | 2/2016 | Manwaring et al. | |
| 9,265,555 B2 | 2/2016 | Manwaring et al. | |
| 9,265,556 B2 | 2/2016 | Manwaring et al. | |
| 9,271,806 B2 | 3/2016 | Tran et al. | |
| 9,283,031 B2 | 3/2016 | Janssen et al. | |
| 9,289,110 B2 | 3/2016 | Woolford et al. | |
| 9,320,560 B2 | 4/2016 | Manwaring et al. | |
| 9,320,563 B2 | 4/2016 | Brustad et al. | |
| 9,393,152 B2 | 7/2016 | Wong et al. | |
| 9,454,896 B2 | 9/2016 | Hocke | |
| 9,475,514 B2 | 10/2016 | Hardy et al. | |

(56) References Cited

U.S. PATENT DOCUMENTS

| | | | |
|---|---|---|---|
| 9,566,108 B2 | 2/2017 | Brustad et al. | |
| 9,579,428 B1 | 2/2017 | Reasoner et al. | |
| 9,597,497 B2 | 3/2017 | Swain et al. | |
| 9,607,508 B2 | 3/2017 | Lint et al. | |
| 9,635,152 B2 | 4/2017 | Ma et al. | |
| 9,730,749 B2 | 8/2017 | Manwaring et al. | |
| 9,901,407 B2 | 2/2018 | Breisacher et al. | |
| 9,936,861 B2 | 4/2018 | Shener-Irmakoglu et al. | |
| 9,962,222 B2 | 5/2018 | Brustad et al. | |
| 9,962,226 B2 | 5/2018 | Brennan et al. | |
| 10,016,248 B2 | 7/2018 | Mirsepassi et al. | |
| 10,060,616 B2 | 8/2018 | Baldwin | |
| 10,076,442 B2 | 9/2018 | Wong et al. | |
| 2002/0173778 A1 | 11/2002 | Knopp et al. | |
| 2002/0183811 A1 | 12/2002 | Irwin | |
| 2004/0059321 A1 | 3/2004 | Knopp et al. | |
| 2004/0236361 A1 | 11/2004 | Sakurai | |
| 2005/0130097 A1 | 6/2005 | Warner | |
| 2005/0130098 A1 | 6/2005 | Warner | |
| 2005/0131436 A1 | 6/2005 | Johnston et al. | |
| 2005/0283148 A1 | 12/2005 | Janssen et al. | |
| 2006/0015041 A1 | 1/2006 | Neal et al. | |
| 2006/0046226 A1 | 3/2006 | Bergler et al. | |
| 2006/0047185 A1* | 3/2006 | Shener | A61B 17/320016 |
| | | | 600/156 |
| 2007/0060921 A1 | 3/2007 | Janssen et al. | |
| 2007/0167943 A1 | 7/2007 | Janssen et al. | |
| 2007/0250098 A1 | 10/2007 | Malackowski et al. | |
| 2007/0282402 A1 | 12/2007 | Irwin | |
| 2008/0086117 A1 | 4/2008 | Cao | |
| 2008/0091061 A1* | 4/2008 | Kumar | A61B 1/00071 |
| | | | 600/104 |
| 2008/0091071 A1* | 4/2008 | Kumar | A61M 3/0208 |
| | | | 600/156 |
| 2008/0114389 A1 | 5/2008 | Johnston et al. | |
| 2008/0294087 A1 | 11/2008 | Steen et al. | |
| 2009/0005712 A1 | 1/2009 | Raney | |
| 2009/0121865 A1 | 5/2009 | Hamel et al. | |
| 2009/0137943 A1* | 5/2009 | Stearns | A61B 17/3421 |
| | | | 604/167.03 |
| 2009/0264881 A1 | 10/2009 | Sakurai | |
| 2009/0270894 A1 | 10/2009 | Rubin et al. | |
| 2010/0036384 A1 | 2/2010 | Gorek et al. | |
| 2010/0069828 A1 | 3/2010 | Steen et al. | |
| 2010/0106146 A1 | 4/2010 | Boitor et al. | |
| 2010/0198200 A1 | 8/2010 | Horvath | |
| 2011/0098531 A1 | 4/2011 | To | |
| 2011/0144636 A1 | 6/2011 | Alexander et al. | |
| 2011/0275027 A1 | 11/2011 | Lint et al. | |
| 2012/0253335 A1 | 10/2012 | Flynn | |
| 2013/0231649 A1 | 9/2013 | Cao | |
| 2013/0245834 A1 | 9/2013 | Laxhuber et al. | |
| 2014/0018782 A1 | 1/2014 | Flynn | |
| 2014/0135617 A1 | 5/2014 | Schoepp | |
| 2014/0243658 A1 | 8/2014 | Breisacher et al. | |
| 2014/0303551 A1* | 10/2014 | Germain | A61B 18/1485 |
| | | | 606/115 |
| 2015/0073399 A1 | 3/2015 | Boitor et al. | |
| 2015/0148615 A1 | 5/2015 | Brennan et al. | |
| 2015/0238682 A1 | 8/2015 | Teranuma et al. | |
| 2015/0257814 A1 | 9/2015 | Berry et al. | |
| 2015/0351831 A1 | 12/2015 | Janssen et al. | |
| 2016/0030102 A1 | 2/2016 | Manwaring et al. | |
| 2016/0030103 A1 | 2/2016 | Manwaring et al. | |
| 2016/0066984 A1 | 3/2016 | Janssen et al. | |
| 2016/0157920 A1 | 6/2016 | Vayser et al. | |
| 2016/0192977 A1 | 7/2016 | Manwaring et al. | |
| 2016/0249971 A1 | 9/2016 | Manwaring et al. | |
| 2016/0256191 A1 | 9/2016 | Tontz | |
| 2016/0258582 A1 | 9/2016 | Gindele et al. | |
| 2016/0278860 A1 | 9/2016 | Cao | |
| 2017/0151011 A1 | 6/2017 | Brustad et al. | |
| 2017/0172583 A1 | 6/2017 | Wildgen et al. | |
| 2017/0212498 A1 | 7/2017 | Laxhuber et al. | |
| 2018/0068870 A1 | 3/2018 | Tsai et al. | |
| 2018/0078301 A1 | 3/2018 | Vayser | |
| 2018/0206902 A1 | 7/2018 | Eggers et al. | |
| 2018/0206909 A1 | 7/2018 | Brustad et al. | |
| 2018/0206938 A1 | 7/2018 | Fayer et al. | |
| 2018/0250088 A1 | 9/2018 | Brennan et al. | |
| 2019/0029755 A1 | 1/2019 | Kubota et al. | |
| 2021/0321999 A1 | 10/2021 | Walen et al. | |

FOREIGN PATENT DOCUMENTS

| | | |
|---|---|---|
| EP | 1796530 B1 | 3/2019 |
| JP | H07502419 A | 3/1995 |
| JP | 2001228868 A | 8/2001 |
| JP | 2007522837 A | 8/2007 |
| JP | 2008511397 A | 4/2008 |
| WO | 9806338 A2 | 2/1998 |
| WO | 9914648 A1 | 3/1999 |
| WO | 0012037 A1 | 3/2000 |
| WO | 2001028446 A1 | 4/2001 |
| WO | 0186369 A1 | 11/2001 |
| WO | 0187198 A1 | 11/2001 |
| WO | 0201310 A1 | 1/2002 |
| WO | 0230308 A1 | 4/2002 |
| WO | 02055149 A2 | 7/2002 |
| WO | 2003079911 A1 | 10/2003 |
| WO | 2003105169 A1 | 12/2003 |
| WO | 2004007023 A1 | 1/2004 |
| WO | 2005060859 A1 | 7/2005 |
| WO | 2005072402 A2 | 8/2005 |
| WO | 2005112737 A1 | 12/2005 |
| WO | 2006009705 A2 | 1/2006 |
| WO | 2006021873 A2 | 3/2006 |
| WO | 2006026685 A2 | 3/2006 |
| WO | 2006039331 A2 | 4/2006 |
| WO | 2007005507 A2 | 1/2007 |
| WO | 2007047128 A1 | 4/2007 |
| WO | 2007084605 A2 | 7/2007 |
| WO | 2007089292 A2 | 8/2007 |
| WO | 2007124380 A1 | 11/2007 |
| WO | 2008014465 A2 | 1/2008 |
| WO | 2008046332 A1 | 4/2008 |
| WO | 2008103519 A2 | 8/2008 |
| WO | 2008103859 A1 | 8/2008 |
| WO | 2008144325 A1 | 11/2008 |
| WO | 2008147771 A1 | 12/2008 |
| WO | 2009042095 A2 | 4/2009 |
| WO | 2009105488 A2 | 8/2009 |
| WO | 2009114367 A2 | 9/2009 |
| WO | 2009124097 A1 | 10/2009 |
| WO | 2010047703 A2 | 4/2010 |
| WO | 2010047966 A1 | 4/2010 |
| WO | 2010054140 A2 | 5/2010 |
| WO | 2010057179 A2 | 5/2010 |
| WO | 2010057183 A2 | 5/2010 |
| WO | 2010120944 A2 | 10/2010 |
| WO | 2011130199 A1 | 10/2011 |
| WO | 2011130236 A1 | 10/2011 |
| WO | 2012013299 A1 | 2/2012 |
| WO | 2012031256 A2 | 3/2012 |
| WO | 2012045095 A1 | 4/2012 |
| WO | 2012139084 A2 | 10/2012 |
| WO | 2013043339 A1 | 3/2013 |
| WO | 2013061038 A2 | 5/2013 |
| WO | 2015081262 A1 | 6/2015 |
| WO | 2015171189 A1 | 11/2015 |
| WO | 2016054140 A1 | 4/2016 |
| WO | 2016081700 A1 | 5/2016 |
| WO | 2016094443 A1 | 6/2016 |
| WO | 2017119487 A1 | 7/2017 |
| WO | 2017139304 A1 | 8/2017 |
| WO | 2018048857 A1 | 3/2018 |

(56)                           References Cited

FOREIGN PATENT DOCUMENTS

WO          2018053229  A1      3/2018
WO          2018201027  A1     11/2018

OTHER PUBLICATIONS

English language abstract for JP 2008-511397 A extracted from espacenet.com database on Jul. 21, 2023, 2 pages.
English language abstract for JPH 07-502419 A extracted from espacenet.com database on Jul. 21, 2023, 2 pages.
English language abstract for WO 2005/112737 A1 extracted from espacenet.com database on Apr. 29, 2021, 2 pages.
English language abstract for WO 2008/046332 A1 extracted from espacenet.com database on Apr. 29, 2021, 1 page.
English language abstract for WO 2017/119487 A1 extracted from espacenet.com database on Apr. 29, 2021, 2 pages.
International Search Report for Application No. PCT/US2019/057599 dated Mar. 24, 2020, 5 pages.
Partial International Search Report for Application No. PCT/US2019/057599 dated Jan. 28, 2020, 2 pages.
English language abstract for JP 2001-228868 A extracted from espacenet.com database and machine-assisted English translation extracted from PAJ database on Jan. 10, 2024, 21 pages.

* cited by examiner

SYSTEMS AND METHODS OF PERFORMING SPINE SURGERY AND MAINTAINING A VOLUME OF FLUID AT A SURGICAL SITE

CROSS-REFERENCE TO RELATED APPLICATIONS

The subject patent application is a Continuation of U.S. National Phase application Ser. No. 17/287,565, filed Apr. 22, 2021, which claims priority to International Application No. PCT/US2019/057599, filed Oct. 23, 2019, which claims priority to and all the benefits of U.S. Provisional Patent Application No. 62/751,964, filed on Oct. 29, 2018, the disclosure of which is hereby incorporated by reference in its entirety.

BACKGROUND

Many surgical procedures involve the resection of bone or tissue with an instrument, often within small bodily orifices or cavities or through small incisions with limited visibility. Of particular interest is minimally invasive surgery (MIS) of the spine. For example, in a transforaminal lumbar interbody fusion (TLIF), an offending intervertebral disc is prepared to receive an interbody spacer with morselized bone to ultimately facilitate fusion of the two vertebrae adjacent the offending disc. With reference to FIG. 1, the preparation of the intervertebral disc may include removing the facet joint to provide access to the intervertebral disc. The annulus fibrosis is resected (i.e., an annulotomy), and at least a portion of the nucleus pulposus contained within the annulus fibrosis is removed (i.e., a discectomy) manually with rongeuers. Moreover, the endplate of each of vertebrae adjacent the intervertebral disc is also prepared, in which a rasp and various curettes are manually deployed to prepare the disc space for receipt of the interbody spacer. In instances where it is contemplated to use a powered surgical instrument as opposed to manual instruments, it is desirable to provide a clear field of view of the endoscope or the operative microscope and reduce heat generated by high-speed variants of powered surgical instruments. Therefore, there is a need in the art for improved systems and methods for performing minimally invasive spine surgery.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

Figure 1:
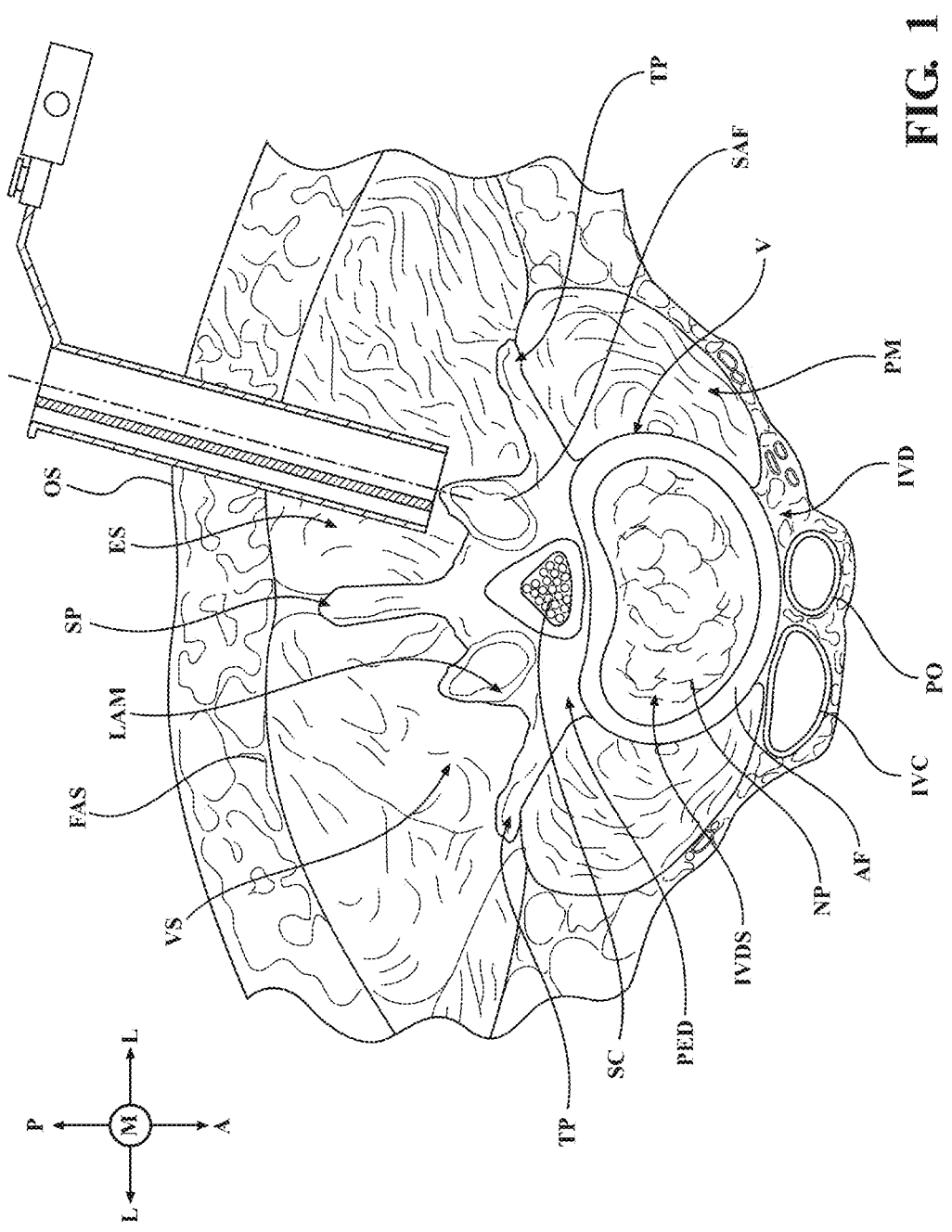
FIG. 1 is an illustration of an axial section of the human spine identifying certain structures and regions. A retractor is positioned within the anatomy to provide a working channel to the surgical site.

FIG. 1 is an illustration of the axial section of the human spine with certain structures and regions to be referenced throughout the present disclosure. With reference to the compass rose of FIG. 1, it is noted that the anatomical directions will also be referenced in accordance with standard medical convention; i.e., medial (M) to the center of the body, lateral (L) to the sides of the body, anterior (A) to the front of the body, and posterior (P) to the rear of the body. The spine includes a series of vertebrae (V) separated by intervertebral discs (IVD). FIG. 1 shows a singular intervertebral disc (IVD) positioned superior a singular vertebra (V) such that the intervertebral disc (IVD) is viewable in plane. A vertebral space (VS) may be considered a volume of the anatomy including the vertebra (V) and adjacent the vertebra (V). Further surrounding the vertebra (V) is various musculature and vasculature. Anterior the anterior aspect of the vertebra (V) and the intervertebral disc (IVD) is the inferior vena cava (IVC) vein and aorta (AO) artery, which serve as the primary cardiovascular vessels of the body. The identified musculature includes the psoas major (PM) generally lateral to the vertebra (V) and the intervertebral disc (IVD), and the erector spinae (ES) generally posterior to the same. Fascia (FAS) and fatty tissue overlay the musculature, and overlying skin (OS) overlays the fascia (FAS).

The vertebra (V) includes the spinous process (SP) and transverse processes (TP) with laminae (LAM) generally extending therebetween. A pedicle (PED) extends between facets (superior articular facet (SAF) identified) and the body of the vertebra (V). The structures collectively form a portion of the vertebra (V) surrounding the spinal cord (SC) extending in the cranial-to-caudal direction. The intervertebral disc (IVD) includes the annulus fibrosis (AF), an outer fibrous ring forming a fibrocartilaginous joint with the vertebra (V) to allow for slight movement while acting as a ligament for holding the vertebrae together. The annulus fibrosis (AF) may define the intervertebral disc space (IVDS), within which the nucleus pulposus (NP) is disposed. The nucleus pulposus (NP) is gel-like in structure and configured to distribute pressure in all directions within the intervertebral disc (IVD) under compressive loads.

Figure 12:
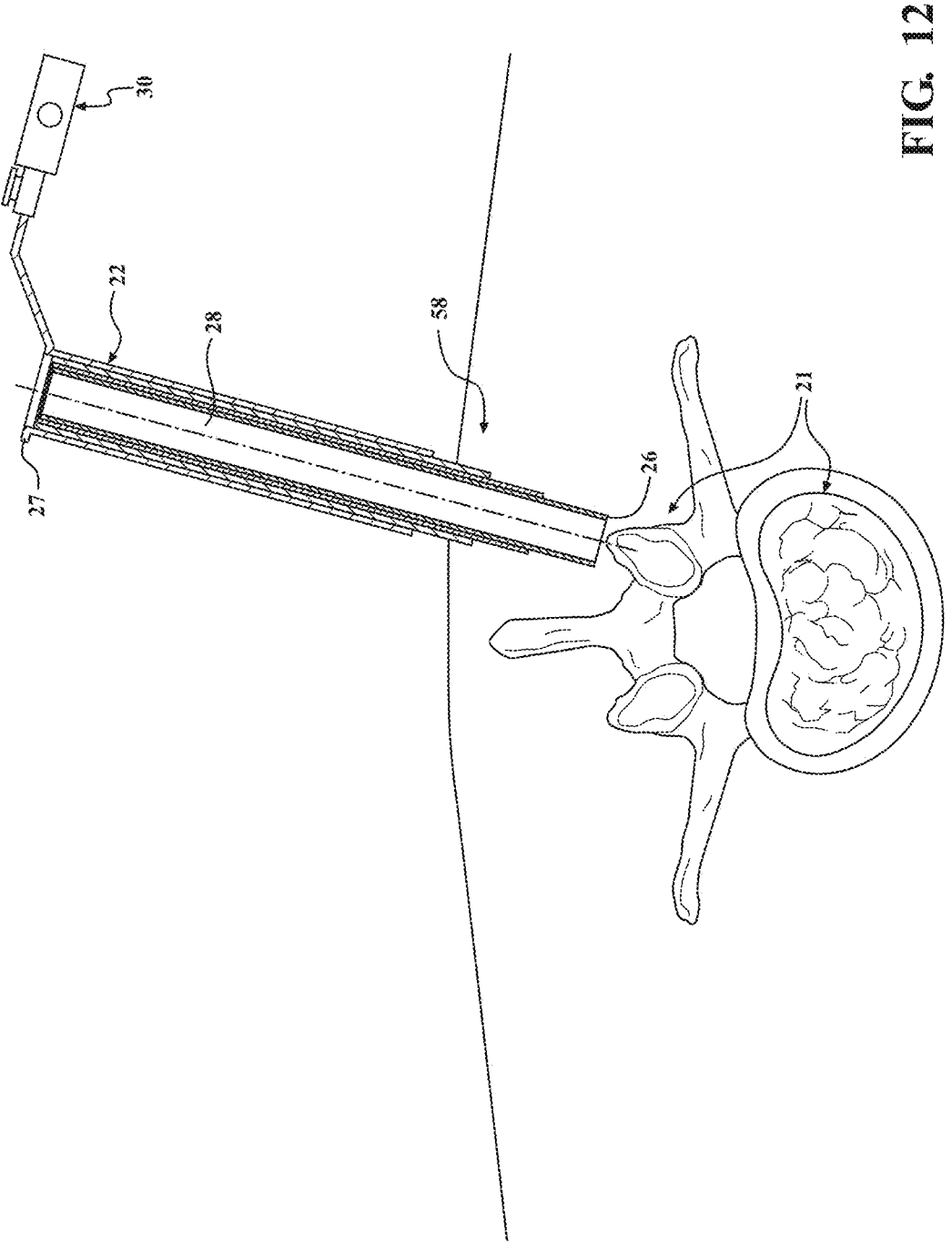
FIG. 12 is an illustration of a method of consecutively positioning a K-wire, followed by a plurality of dilators, followed by a retractor.
Figure 13:
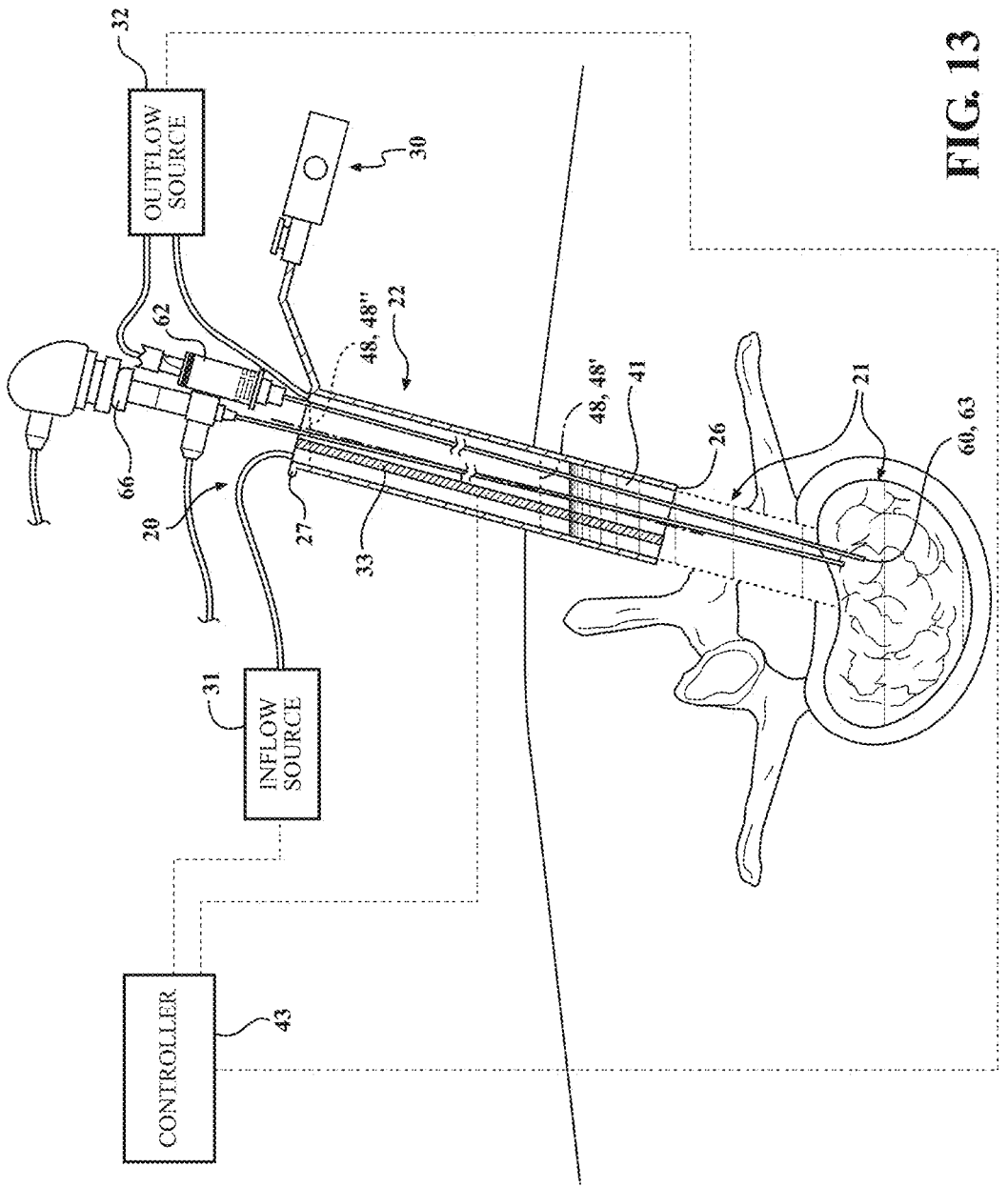
FIG. 13 is an illustration of a method of using the surgical system including a step of an endoscope.

As mentioned, of particular interest is the preparation of the intervertebral disc space (IVDS) with a minimally invasive approach. As is common to MIS, and is illustrated in FIG. 12, positioned consecutively are a K-wire (not shown), a plurality of dilators 58, and a retractor 22 to provide a working channel 28 to a surgical site 21 at the region of interest. While some visualization may be realized through the working channel 28 provided through the retractor 22, it is readily appreciated that meaningful visualization within the intervertebral disc space (IVDS) or vertebral space (VS) may be unachievable, in particular, the lateral aspects and the posterior aspect, for example. Further, even with placement of a visualization device that may be capable of accessing the aforementioned areas (such as an endoscope, for example), blood and bone debris may obstruct the field of view, particularly after resection of the tissue with the use of a surgical instrument 62, such as shown in FIG. 13.

Figure 2:
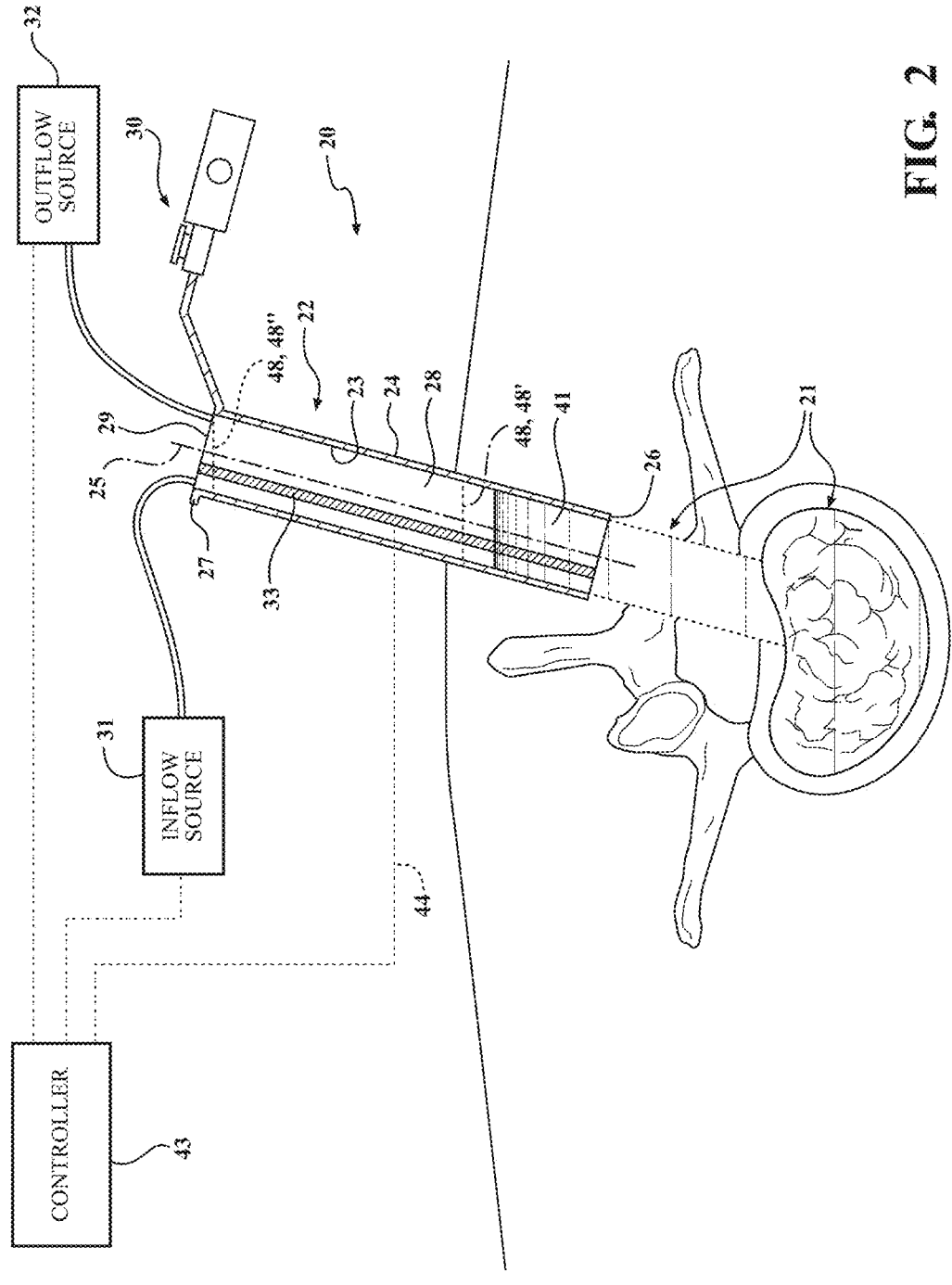
FIG. 2 is an illustration of a first variation of the surgical system including a retractor, an inflow source, an outflow source, a controller, and a sensor for maintaining a threshold level of fluid in the retractor and the surgical site.

Referring now to FIG. 2, a surgical system 20 in accordance with a first variation of the present disclosure is shown. The surgical system 20 may include a retractor 22 having a proximal end 27, a distal end 26, an inner surface 23, an outer surface 24, and a central axis 25 extending between the distal end 26 and the proximal end 27, in which the distal end 26 is configured to be positioned within the patient to provide a working channel 28 to the surgical site 21 and the proximal end 27 defines an opening 29 open to ambient. In some variations, such as when the operation being performed is a transforaminal lumbar interbody fusion (TLIF), the distal end 26 of the retractor 22 may be positioned adjacent to the intervertebral disc space (IVDS) after the removal of the facet joint to provide access to the intervertebral disc for resection of desired tissue. Additionally, in some endoscopic procedures, such as those pertaining to the spine, the surgical site 21 cannot be subjected to substantial barometric pressure. In some instances, the surgical site 21 may not be pressurized due to physiological constraints within the region, while in other instances it may be impractical. Therefore, in certain variations, the opening 29 of the retractor 22 is open to ambient to prevent exposing the surgical site 21 to greater than atmospheric pressures by allowing excess matter (air, for example) in the retractor 22 to escape through the opening 29 as opposed to building up pressure within the surgical site 21.

Figure 14:
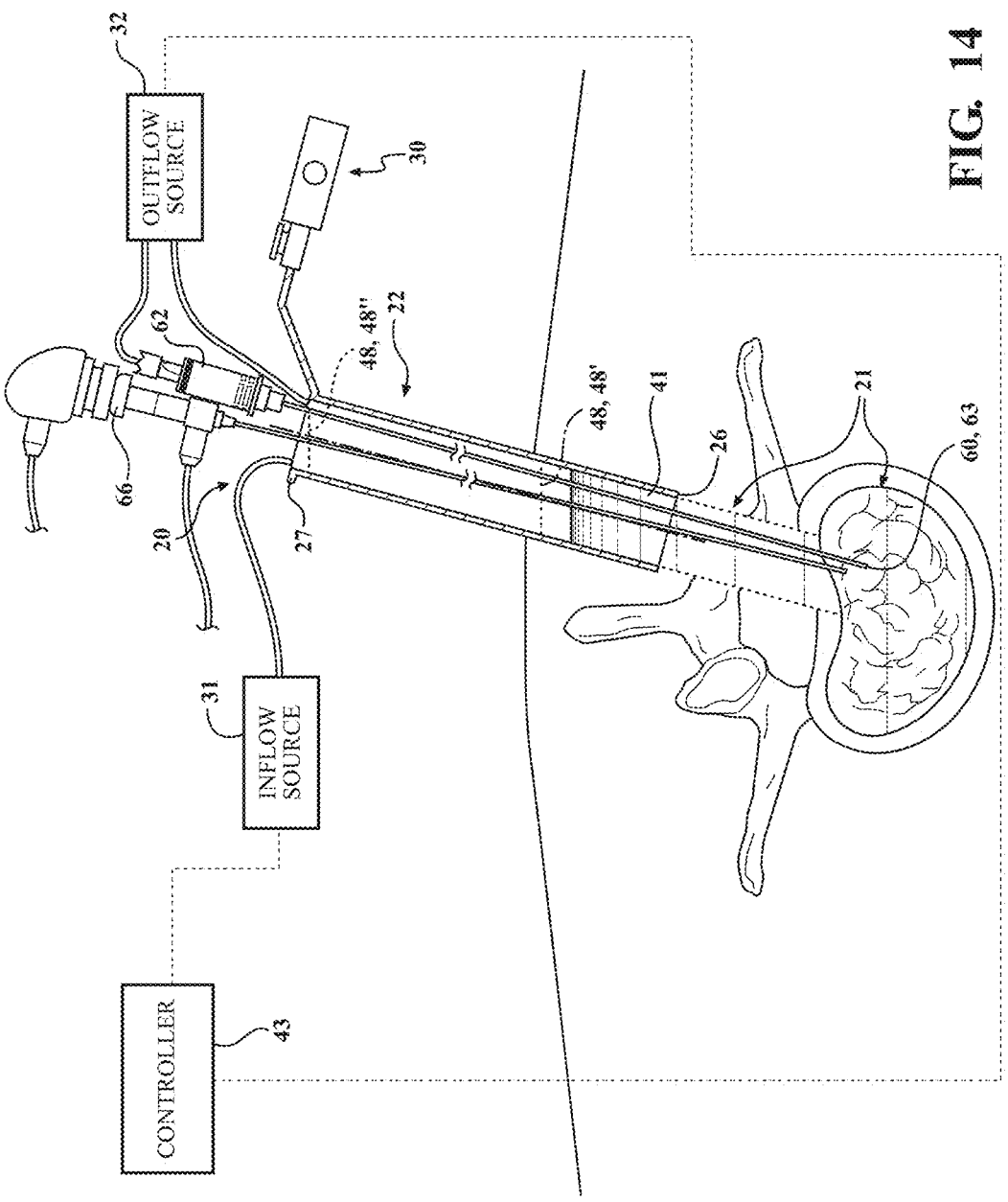
FIG. 14 is an illustration of a method of using the surgical system including an endoscope and a surgical instrument.

The surgical system 20 may also include an inflow source 31 in fluid communication with the retractor 22 for providing a fluid to the surgical site 21 to form a volume of fluid 41 disposed in the surgical site 21 and the retractor 22, as well as an outflow source 32 in fluid communication with the retractor 22 for removing a volume of fluid from the surgical site. An exemplary inflow source is disclosed in U.S. Pat. No. 7,238,010, which is hereby incorporated by reference in its entirety. The inflow source 31 and/or the outflow source 32 may include, for example, a vacuum source, or a positive pressure pump, such as a peristaltic pump. The inflow source 31 and the outflow source 32 may be in fluid communication with the retractor by tubing coupled to the retractor 22, for example. In certain configurations, the fluid is a suitable fluid such as water, saline, and the like, preferably a liquid. Among other advantages, the volume of fluid 41 may improve visualization of the surgical site 21 from an endoscope 66 or improve cooling of a surgical instrument 62 and the nearby tissue, illustrated in FIG. 14.

With continued reference to FIG. 2, the surgical system 20 may further include a sensor 33 coupled to the retractor 22 for providing a sensor input signal 44 based on a level of fluid disposed in the retractor 22. The level of fluid may pertain to a height or a volume of the fluid extending up the retractor 22 from the distal end 26. The surgical system 20 may also further include a controller 43 in communication with at least one of the sensor 33, the inflow source 31, or the outflow source 32 to control a flow rate of fluid being provided to the surgical site 21 by the inflow source 31, an outflow rate of fluid being removed from the surgical site 21 by the outflow source 32, or a combination thereof based on the sensor input signal 44, such that a threshold level of fluid 48 is maintained in the retractor 22 and at the surgical site 21. The threshold level of fluid 48 pertains to a desired range of fluid to be maintained in the retractor 22 and includes at least one of a minimum threshold 48' or a maximum threshold 48". The minimum threshold 48' may be defined such that it ensures a desired minimum level of fluid is at the surgical site 21 and within the retractor 22 during operation of the surgical system 20. For example, the minimum threshold 48' may be defined such that the fluid level is maintained at or above the distal end 26 of the retractor 22, for example, one-third, one-half, or three-quarters upwardly along the central axis 25 of the retractor 22. In another example, minimum threshold 48' may be an approximate minimum steady state volume of fluid to be maintained within the retractor 22, for example, 0.5 mL, 0.1 mL, 1 mL, 5 mL, etc. The maximum threshold 48" may be defined, for example, such that it ensures fluid does not overflow from the retractor 22 during operation of the surgical system 20.

Still referring to FIG. 2, the controller 43 may be configured to receive a user input signal corresponding to the threshold level of fluid 48 disposed in the retractor 22 for controlling the outflow source 32 and/or the inflow source 31 based on the user input signal. For example, the user input signal may pertain to the desired level of fluid to be maintained at the surgical site 21 and within the retractor 22 during operation of the surgical system 20. The user input signal may be provided by a user input device (not shown), such as a button, GUI, knob, slider, etc. that provides the operator with an interface capable of providing the user input signal to the controller 43 in order to modulate operational parameters of the surgical system 20, such as the threshold level of fluid 48.

In an example of the operational behavior of the surgical system 20, a user input signal pertaining to an increase in the threshold level of fluid 48 received by the controller 43 may result in the controller 43 controlling the outflow source 32 to temporarily decrease the outflow rate, while also controlling the inflow source 31 to maintain the inflow flow rate. Alternatively, for example, the controller 43 may control the inflow source 31 to temporarily increase the inflow flow rate while controlling the outflow source 32 to maintain the outflow rate in order to maintain the volume of fluid 41 within the increased threshold level of fluid 48.

Conversely, a user input signal pertaining to a decrease in the threshold level of fluid 48 provided to the controller 43 may result in the controller 43 controlling the outflow source 32 to temporarily increase the outflow rate while controlling the inflow source 31 to maintain the inflow flow rate. Alternatively, for example, the controller 43 may control the inflow source 31 to temporarily decrease the inflow flow rate while controlling the outflow source 32 to maintain the outflow rate in order to maintain the volume of fluid 41 within the decreased threshold level of fluid 48.

Additionally or alternatively, the controller 43 may also be configured to receive a user input signal pertaining to a turnover rate of fluid disposed in the retractor 22. Based on the user input signal pertaining to the turnover rate, the controller 43 is capable of controlling at least one of the outflow source 32 or the inflow source 31. The turnover rate of the fluid disposed in the retractor 22 may pertain to a synchronized inflow rate of fluid to the surgical site 21 coordinated with the outflow rate from the surgical site 21 to ensure a continuous supply of fresh fluid to the surgical site 21 to clear any debris and facilitate clear visualization. For example, with the coordinated inflow rate and outflow rate of fluid being provided, a swirling motion of the fluid in the surgical site 21 may result that moves debris away from surgical site 21.

The turnover rate may be adjusted up or down by the user based on situational needs. For example, a user input signal pertaining to an increase in the turnover rate may result in the controller 43 controlling the outflow source 32 and the inflow source 31 to increase the outflow rate and the inflow rate, respectively. The increase in the turnover rate may be advantageous for situations where the debris being generated at the surgical site 21 is not evacuated from the surgical site 21 as quickly as desired.

Conversely, a user input signal pertaining to a decrease in the turnover rate may result in the controller 43 controlling the outflow source 32 and the inflow source 31 to decrease the outflow rate and the inflow rate, respectively. The decrease in the turnover rate may be advantageous for situations where little debris is being generated at the surgical site 21, and the swirling motion of the fluid unnecessarily obstructs visualization.

Figure 3:
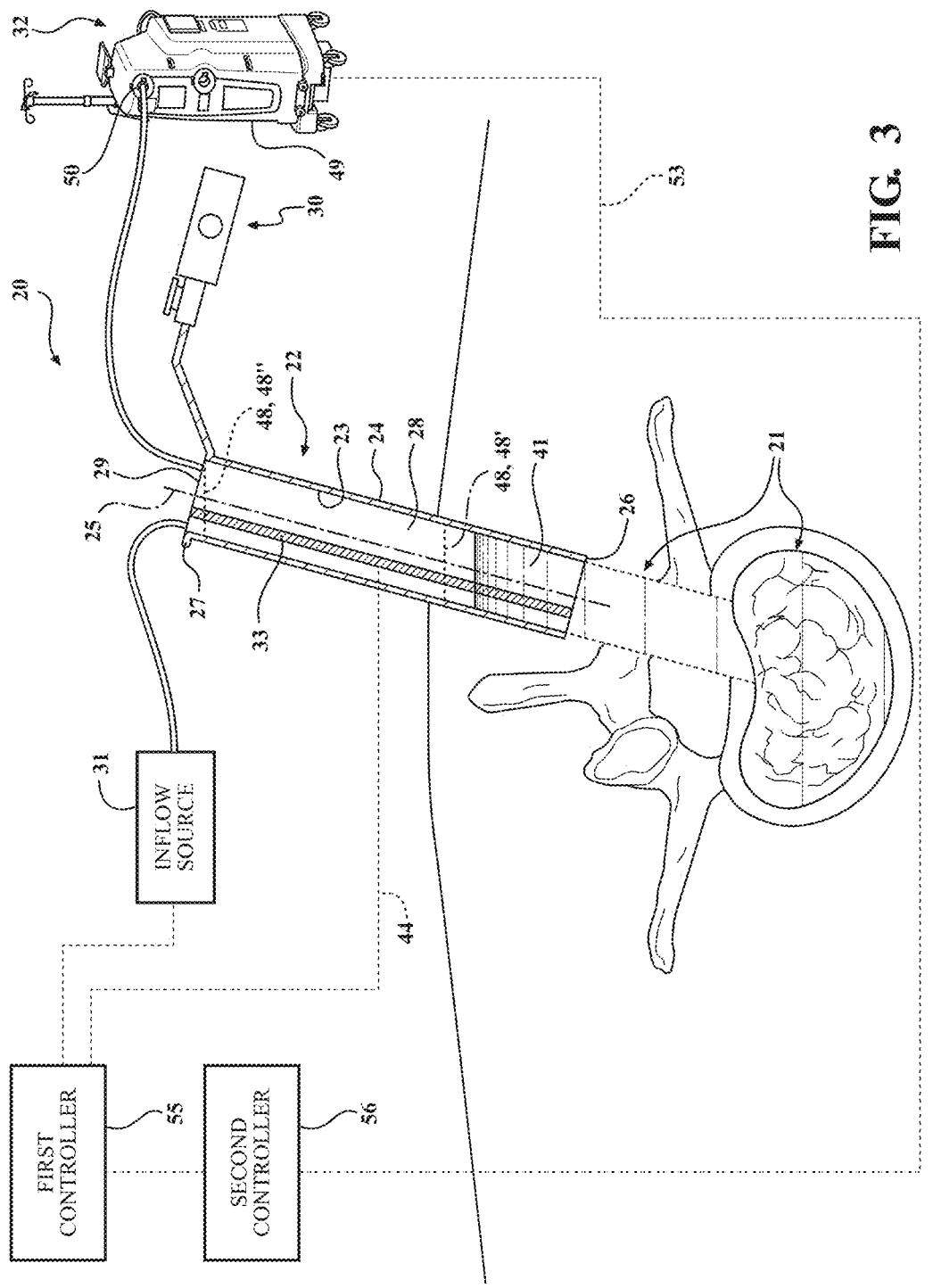
FIG. 3 is an illustration of a second variation of the surgical system including a second controller in communication with an outflow source.

Referring to FIG. 3, in a second variation, the surgical system 20 may include, amongst other components, an outflow source 32 in fluid communication with the retractor 22 for removing a volume of fluid and having an outflow sensor 50 for providing an outflow input signal 53. In certain configurations, the outflow source 32 may be a vacuum system 49. The vacuum system 49, for example, may be a surgical waste management system sold under the tradename NEPTUNE manufactured by Stryker Corporation (Kalamazoo, Mich.) and disclosed in commonly owned U.S. Pat. Nos. 7,621,898; 8,216,199; 8,740,866; 8,915,897; 9,579,428, among others, each of which is hereby incorporated by reference in its entirety. The outflow sensor 50 may be a pressure sensor, flowrate sensor, or a combination thereof and may be used to generate the outflow input signal 53 pertaining to operational characteristics of the outflow source 32. For example, the operational characteristics of the outflow source 32 may include a pressure differential being generated by outflow source 32 or a mass/volumetric flowrate of matter being removed from the surgical site 21 by the outflow source 32.

The surgical system 20 of the aforementioned second variation may further include a fluid level sensor 33 (similar to the aforementioned sensor of the first variation), a first controller 55, and a second controller 56 in communication with the first controller 55 and the outflow source 32, such that the first controller 55 controls the inflow source 31 based on the received outflow input signal 53 and the fluid level sensor input signal 44. In certain variations, the first controller 55 is in communication with at least one of the inflow source 31, or the outflow source 32 to control a flow rate of fluid being provided by the inflow source 31, an outflow rate of fluid being removed by the outflow source 32, or a combination thereof based on the fluid level sensor input signal 44 and the outflow input signal 53. For example, the outflow input signal 53 may be provided to the controller(s) to provide feedback regarding the operational characteristics of the outflow source 32 in order to compensate for the operation of the outflow source 32 in order to maintain the threshold level of fluid 48 in the retractor 22.

Advantageously, the aforementioned feedback allows the controller(s) to anticipate changes in the level of fluid 41 due to the operation of the outflow source 32 faster than could be detected by the fluid level sensor 33. More specifically, changes in the operational characteristics of the outflow source 32 precede any resulting change in the level of fluid 41 in the retractor 22. Thus, the fluid level sensor 33 may experience a delay in conveying a change in the level of fluid in the retractor 22 in response to a change in an operational characteristic of the outflow source 32. Therefore, the provided feedback of the operational characteristics of the outflow source 32 facilitates a smoother response to transient operation of the surgical system 20.

Figure 4:
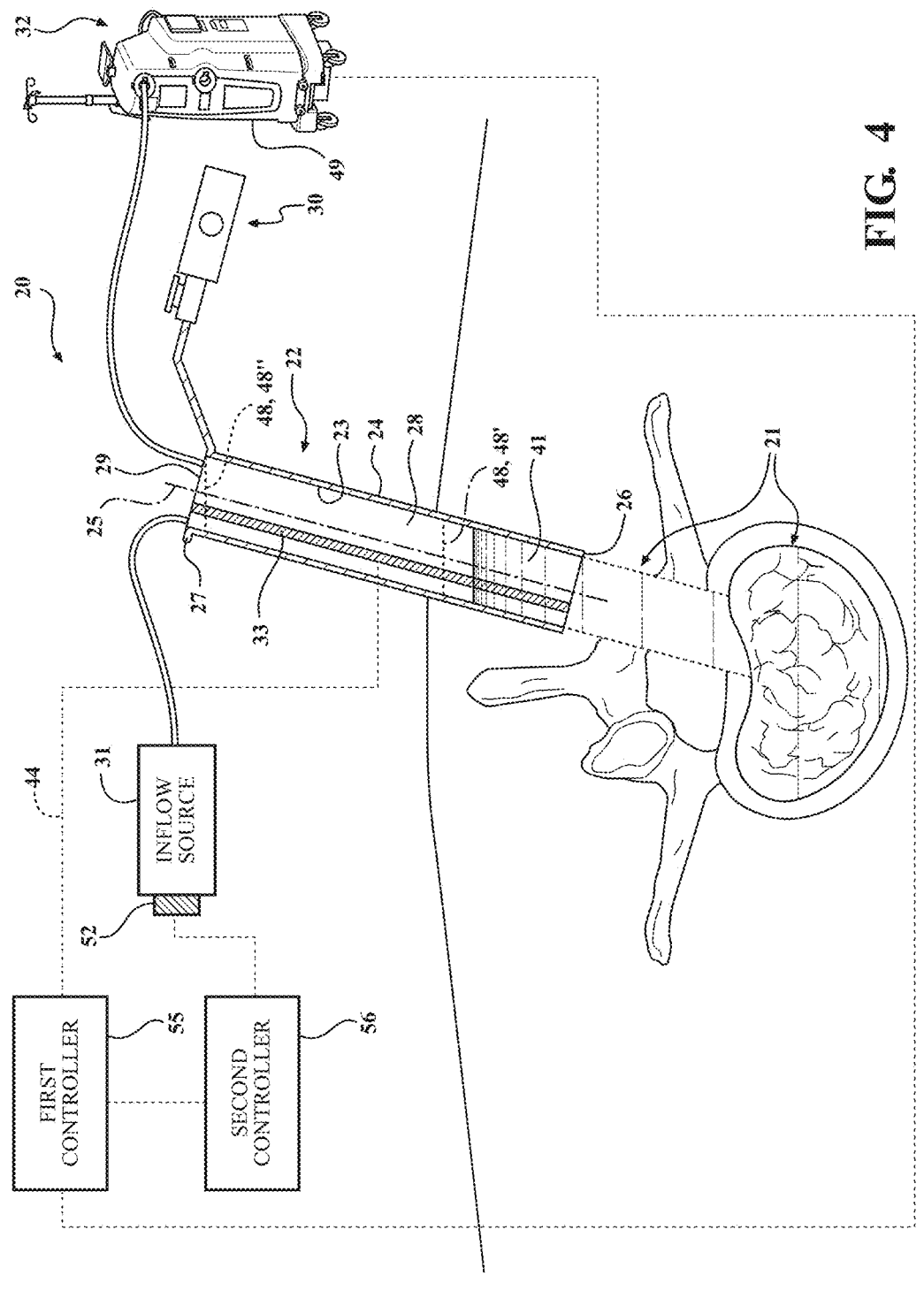
FIG. 4 is an illustration of a third variation of the surgical system including a second controller in communication with an inflow source.

In a third variation, illustrated in FIG. 4, the surgical system 20 may include, amongst other components, an inflow source 31 having an inflow sensor 52 for providing an inflow input signal 57, and an outflow source 32 (similar to aforementioned outflow source in previous variations) for removing a volume of fluid from the surgical site 21. The inflow sensor 52 may include a pressure sensor, flowrate sensor, or a combination thereof and may be used to generate the inflow input signal 57 pertaining to operational characteristics of the inflow source 31. For example, the operational characteristics of the inflow source 31 may include a pressure differential being generated by the inflow source 31 or a mass/volumetric flowrate of fluid being provided to the surgical site 21 by the inflow source 31.

The surgical system 20 of the aforementioned third variation may also include the fluid level sensor 33 (similar to aforementioned fluid level sensor in previous variations) coupled to the retractor 22 for providing a fluid level sensor input signal 44 responsive to the level of fluid 41 in the retractor 22, a first controller 55, and a second controller 56 in communication with the first controller 55 and the inflow source 31, such that the first controller 55 controls the outflow source 32 based on the inflow input signal 57 and the fluid level sensor input signal 44. In certain variations, the first controller 55 is in communication with at least one of the inflow source 31, or the outflow source 32 to control a flow rate of fluid being provided by the inflow source 31, an outflow rate of fluid being removed by the outflow source 32, or a combination thereof based on the fluid level sensor input signal 44 and the inflow input signal 57. For example, the inflow input signal 57 may be provided to the controller(s) to provide feedback regarding the operational characteristics of the inflow source 31 in order to compensate for the operation of the inflow source 31 in order to maintain the threshold level of fluid 48 in the retractor 22.

Advantageously, the aforementioned feedback allows the controller(s) to anticipate changes in the level of fluid 41 due to the operation of the inflow source 31 faster than could be detected by the fluid level sensor 33. More specifically, changes in the operational characteristics of the inflow source 31 precede any resulting change in the level of fluid 41 in the retractor 22. Thus, the fluid level sensor 33 may experience a delay in conveying a change in the level of fluid in the retractor 22 in response to a change in an operational characteristic of the inflow source 31. Therefore, the provided feedback of the operational characteristics of the inflow source 31 facilitates a smoother response to transient operation of the surgical system 20.

Figure 5:
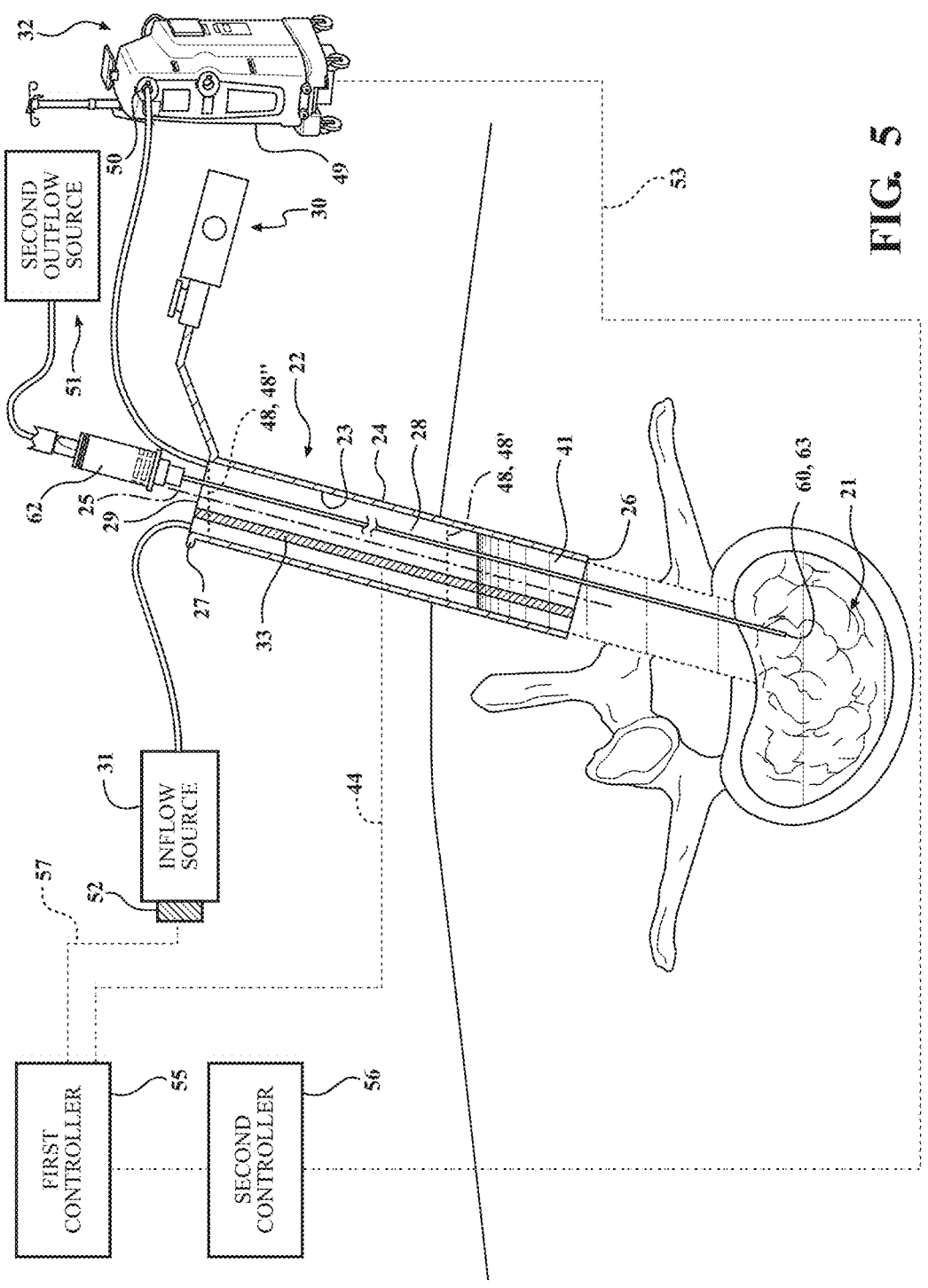
FIG. 5 is an illustration of a fourth variation of the surgical system including a first outflow source and a second outflow source.

In a fourth variation, illustrated in FIG. 5, the surgical system 20 may include, amongst other components, an inflow source 31 having an inflow sensor 52 for providing an inflow input signal 57, and a first outflow source 32 (similar to aforementioned outflow source in previous variations) in fluid communication with the retractor 22 for removing a volume of fluid from the surgical site 21 and having an outflow sensor 50 for providing an outflow input signal 53. The surgical system 20 may also include a second outflow source 51 that may be in fluid communication with an outflow outlet 63 of a surgical instrument 62 having a cutting member 60 for removing a volume of fluid from the surgical site 21. In certain variations, the second outflow source 51 may be, for example, a centralized wall suction system, which in some configurations may not be controllable by the surgical system 20. The surgical system 20 may further include a second controller 56 in communication with the first controller 55 and the first outflow source 32 such that the first controller 55 controls the inflow source 31 to control a flow rate of fluid being provided by the inflow source 31 and the second controller 56 controls the first outflow source 32 to control an outflow rate of fluid being removed by the first outflow source 32 based on at least one of the sensor input signal 44, the inflow input signal 57, or the outflow input signal 53 such that a threshold level of fluid 48 is maintained in the retractor 22 to compensate for sensed changes due to operation of the second outflow source 51.

In an illustrative scenario, with the inflow source 31 and first outflow source 32 being controlled by the controller 43 to maintain a threshold amount of fluid 48 in the retractor 22 and the surgical site 21, the user may insert the surgical instrument 62 in fluid communication with the second outflow source 51, for example, a shaver coupled to a vacuum. Because the second outflow source 51 may be electronically independent of the first outflow source 32, the controller 43 may not anticipate the suction associated with the shaver being introduced into the volume of the fluid 41. The insertion of the shaver and operation of the vacuum may initially decrease rapidly the level of fluid 41 disposed in the retractor 22. It is important that the volume of the fluid 41 not be entirely aspirated such that no fluid remains. Therefore, the controller 43 is configured to compensate for this in a rapid and responsive manner. The controller 43 may do so by increasing the inflow rate of the inflow source 31, decreasing the outflow rate of the first outflow source 32, or a combination thereof. The new parameter(s) may be maintained while the shaver remains operational within the anatomy. Similarly, once the shaver is removed from the retractor 22, the new parameter(s), if left unchanged, may result in an undesired amount of fluid rapidly accumulating within the retractor 22 or overflowing from the retractor 22. The controller 43 is configured to rapidly and responsively compensate for this by decreasing the inflow rate of the inflow source 31, increasing the outflow rate of the first outflow source 32, or a combination thereof. The aforementioned functionality advantageously provides for ensuring the minimum threshold of fluid 48' is maintained in the retractor 22, and the maximum threshold of fluid 48" is not exceed without requiring specific user intervention or input. In other words, the surgeon need not stop the procedure to adjust the parameter(s) of the surgical system 20 prior to insertion or removal of the shaver. Furthermore, the functionality may be particularly well suited with off-the-shelf or standalone surgical instruments that are configured to be operated independently (i.e., not electronically integrated into the surgical system 20).

While in some variations, multiple controllers are used to operate various components of the surgical system 20, it is contemplated that a single controller, for example having a plurality of sub-controllers, could be used to provide a similar capability.

Figure 7:
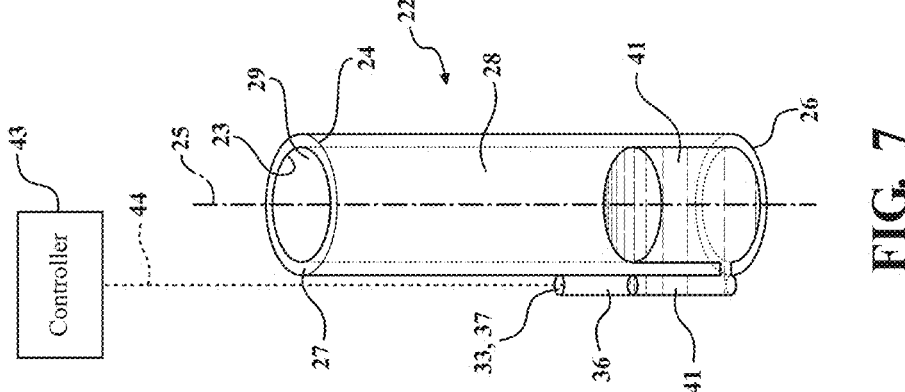
FIG. 7 is an illustration of another configuration of the sensor including a measurement vessel in fluid communication with the retractor and a pressure sensor coupled to the measurement vessel.
Figure 6:
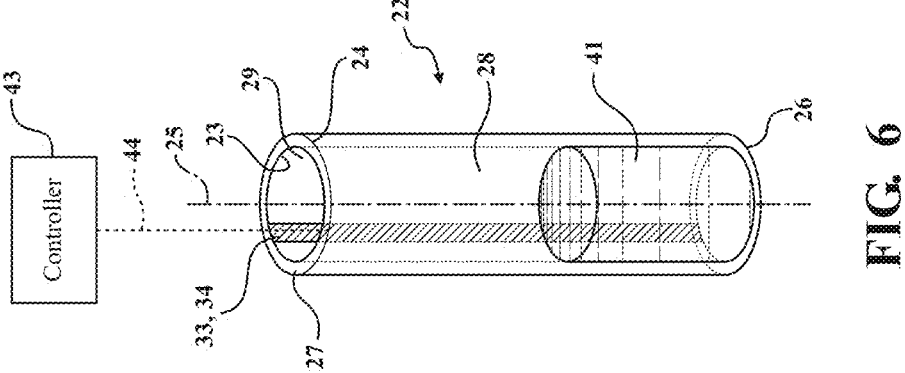
FIG. 6 is an illustration of one configuration of the sensor including an electrical fluid sensing member coupled to the retractor.

Referring now to FIG. 6, in one variation, the aforementioned sensor 33 may include an electrical fluid sensing member 34 disposed about the inner surface 23 or outer surface 24 of the retractor 22 and provides the sensor input signal 44 to the aforementioned controller(s). The electrical fluid sensing member 34 may be configured to sense impedance or resistance, such as the impedance or resistance of liquid in the retractor 22. In an additional variation, shown in FIG. 7, the retractor 22 may further include a measurement vessel 36 in communication with the retractor 22 and the sensor 33 includes a pressure sensor 37 that is configured to measure pressure within the measurement vessel 36 and provides the sensor input signal 44 to the aforementioned controller(s). In certain variations, the sensor input signal 44 may pertain to the height or volume of the fluid extending up the retractor 22 ascertained by the sensor 33. The aforementioned controller(s) may compare the threshold level of fluid 48 and the sensor input signal 44, and based on the comparison of the threshold level of fluid 48 and the sensor input signal 44, the controller(s) may control at least one of the outflow source 32 or the inflow source 31 to maintain the volume of fluid 41 within the threshold level of fluid 48.

Figure 8:
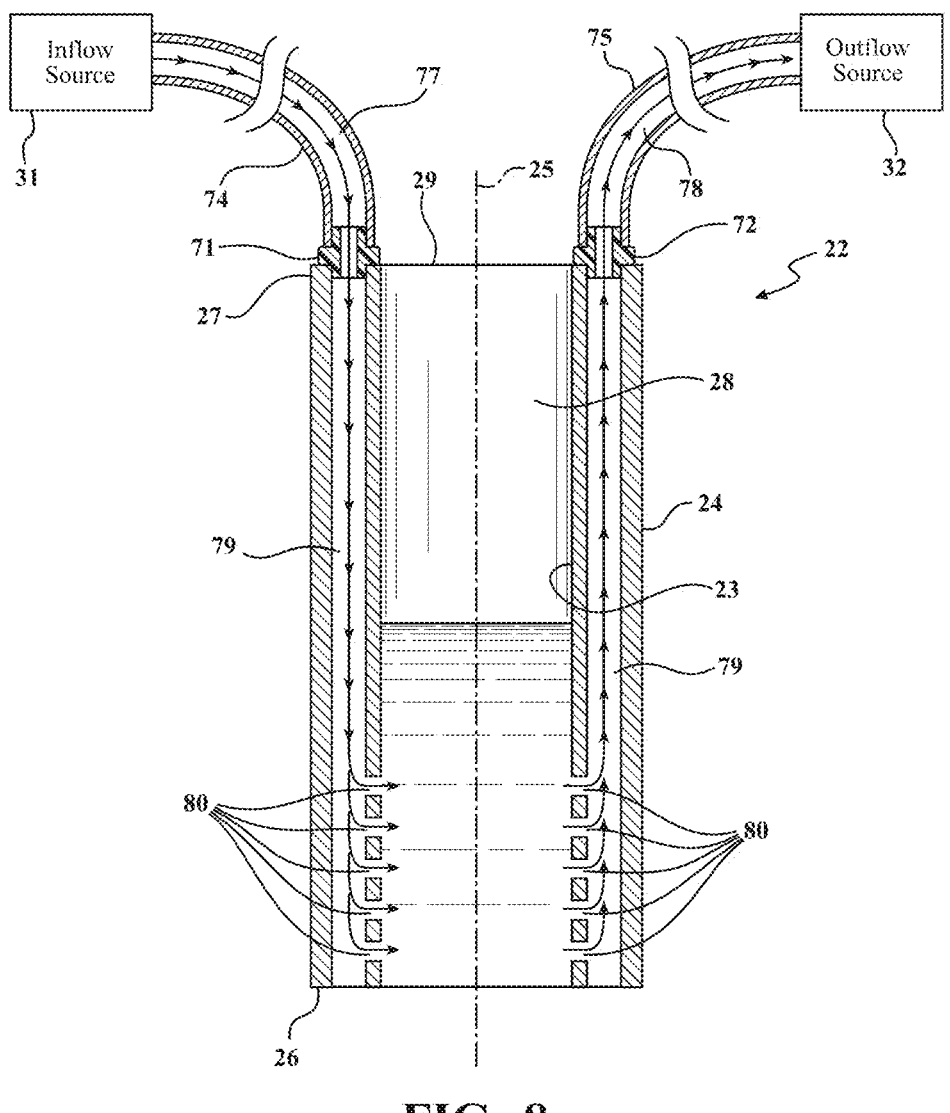
FIG. 8 is an cross-sectional illustration of one configuration of the retractor, including an inflow-outflow channel defined between the inner and outer surface of the retractor.

Referring now to FIG. 8, a variation of the retractor 22 is shown. The retractor 22 may include at least one of an inflow port 71 or an outflow port 72. The inflow port 71 is adapted to receive an inflow tube 74 in fluid communication with an inflow source 31 to define an inflow path 77, and the outflow port 72 is adapted to be coupled to an outflow tube 75 in fluid communication with an outflow source 32 to define an outflow path 78. FIG. 8 shows the inflow port 71 and the outflow port 72 coupled to the retractor 22, and more particularly near the distal end 26 of the retractor 22. For illustrative purposes, the inflow port 71 and outflow port 72 are positioned on opposite sides of the retractor 22, but other locations and arrangements are within the scope of the present disclosure. The inflow port 71 and outflow port 72 are adapted to be removably coupled to the inflow tube 74 and outflow tube 75, respectively, with a Luer fitting, or other suitable connection providing fluid communication between the inflow source 31 and outflow source 32, respectively.

FIG. 8 shows the retractor 22 defining an inflow-outflow channel 79 at least partially separate from the working channel 28. The inflow-outflow channel 79 of the illustrated variation is defined between the inner surface 23 and the outer surface 24 of the retractor 22. In other words, the inflow-outflow channel 79 may be an annular space extending between the inner surface 23, the outer surface 24, and the distal and proximal ends 26, 27 of the retractor 22. The inflow-outflow channel 79 at the proximal end 27 is adapted to be placed in fluid communication with at least one of the inflow port 71 or the outflow port 72. The inflow-outflow channel 79 at the distal end 26 may be open such that the fluid flows out the distal end 26. In the variation illustrated in FIG. 8, the inflow-outflow channel at the distal end 26 is closed, and the inner surface 23 includes fenestrations 80 providing fluid communication between the inflow-outflow channel 79 and the working channel 28. The fenestrations 80 may be, for example, apertures circumferentially arranged about at least a portion of the inner surface 23, and in particular, a lower portion of the inner surface as shown in FIG. 8. FIG. 8 shows the inflow-outflow channel 79 in fluid communication with each of the inflow tube 74 and the outflow tube 75. In one variant, the annular space defining the inflow-outflow channel may include partitions (not shown) extending a length of the retractor 22 such that the partitions provide fluid separation between the inflow fluid being received from the inflow tube 74, and the fluid to be removed by the outflow tube 75.

Figure 9:
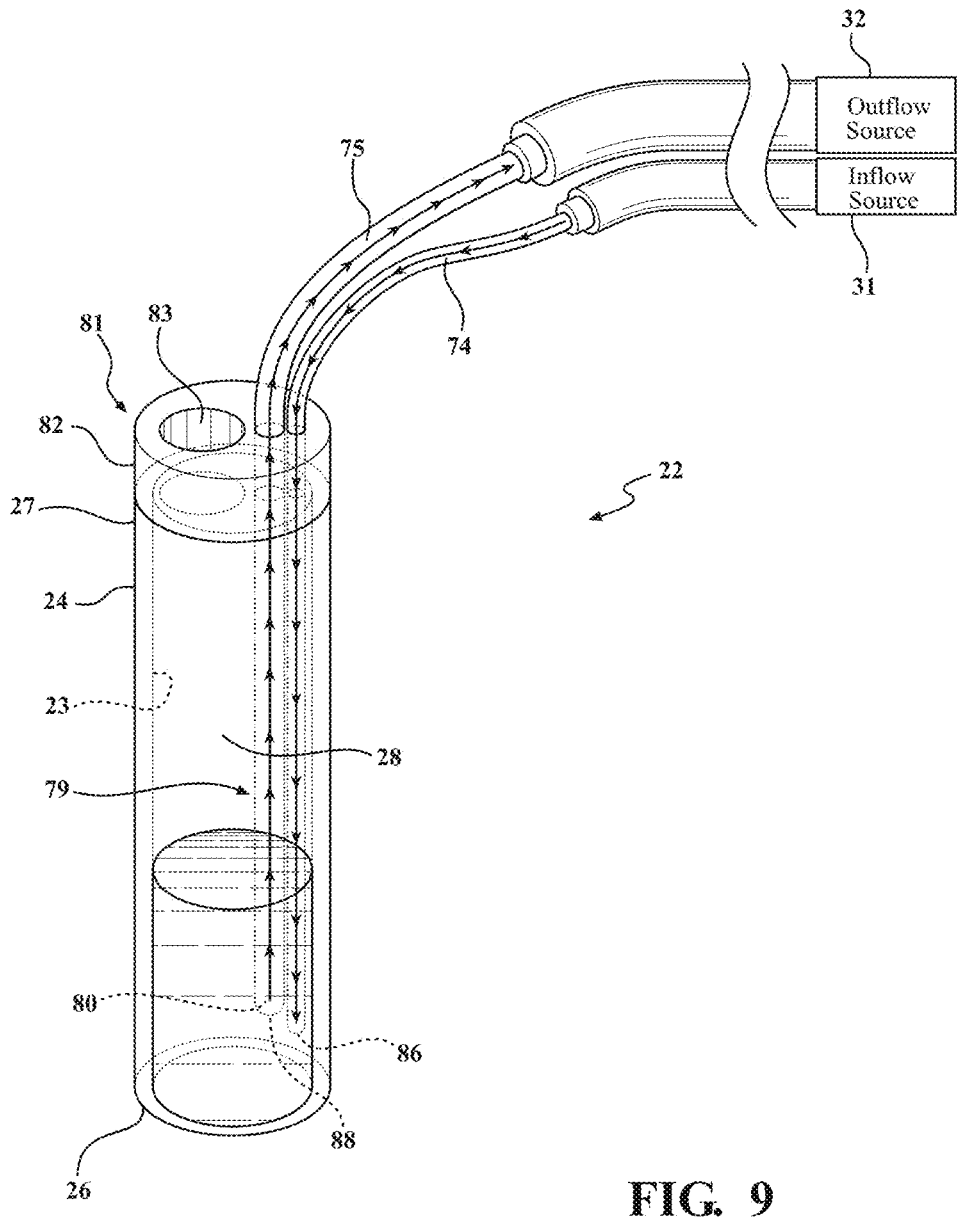
FIG. 9 is an perspective view illustration of one configuration of the retractor including a coupling member and an inflow-outflow channel defined by inflow and outflow tubes disposed near the inner surface of the retractor.

It is contemplated that other manners for providing fluid communication between the inflow-outflow channel 79 and the retractor 22 are contemplated. The retractor 22 may also include a coupling member 81 configured to be coupled to the retractor 22, as shown in FIG. 9. The coupling member 81 may be a plug 82 sized to be snugly inserted within the working channel 28 of the retractor 22 and secured by interference fit. An access opening 83 may be defined through the coupling member 81 with the access opening 83 suitably sized to receive one or more surgical instruments, for example, the cutting instrument 62 or the endoscope 66. The retractor 22 may also further include an inflow tube 74 and an outflow tube 75 each coupled to the coupling member 81. Each of the inflow and outflow tubes 74, 75 extend distally from the coupling member 81. A distal end 86 of the inflow tube 74 is spaced at a desired distance from the coupling member 81, for example near the distal end 26 of the retractor 22. Likewise, a distal end 88 of the outflow tube 75 is spaced at a desired distance from the coupling member 81, for example near the distal end 26 of the retractor 22. FIG. 9 shows the distal end 86 of the inflow tube 74 positioned distal to the distal end 88 of the outflow tube 75. The arrangement may facilitate the outflow tube 75 siphoning the debris-filled fluid from the retractor 22 with the inflow tube 74 providing the fresh fluid closer to the surgical site 21. The arrangement may also provide the aforementioned swirling effect to move debris away from the field of view of the endoscope 66. In the illustrated embodiment, the inflow and outflow tubes 74,75 are positioned in a side-by-side configuration, and further positioned near the inner surface 23 of the retractor 22. With the inflow and outflow tubes 74,75 positioned near the inner surface 23, substantially an entirety of the working channel 28 remains unobstructed for the passage of, among other items, the surgical instrument 62 and/or the endoscope 66 through the access opening 83.

Figure 10:
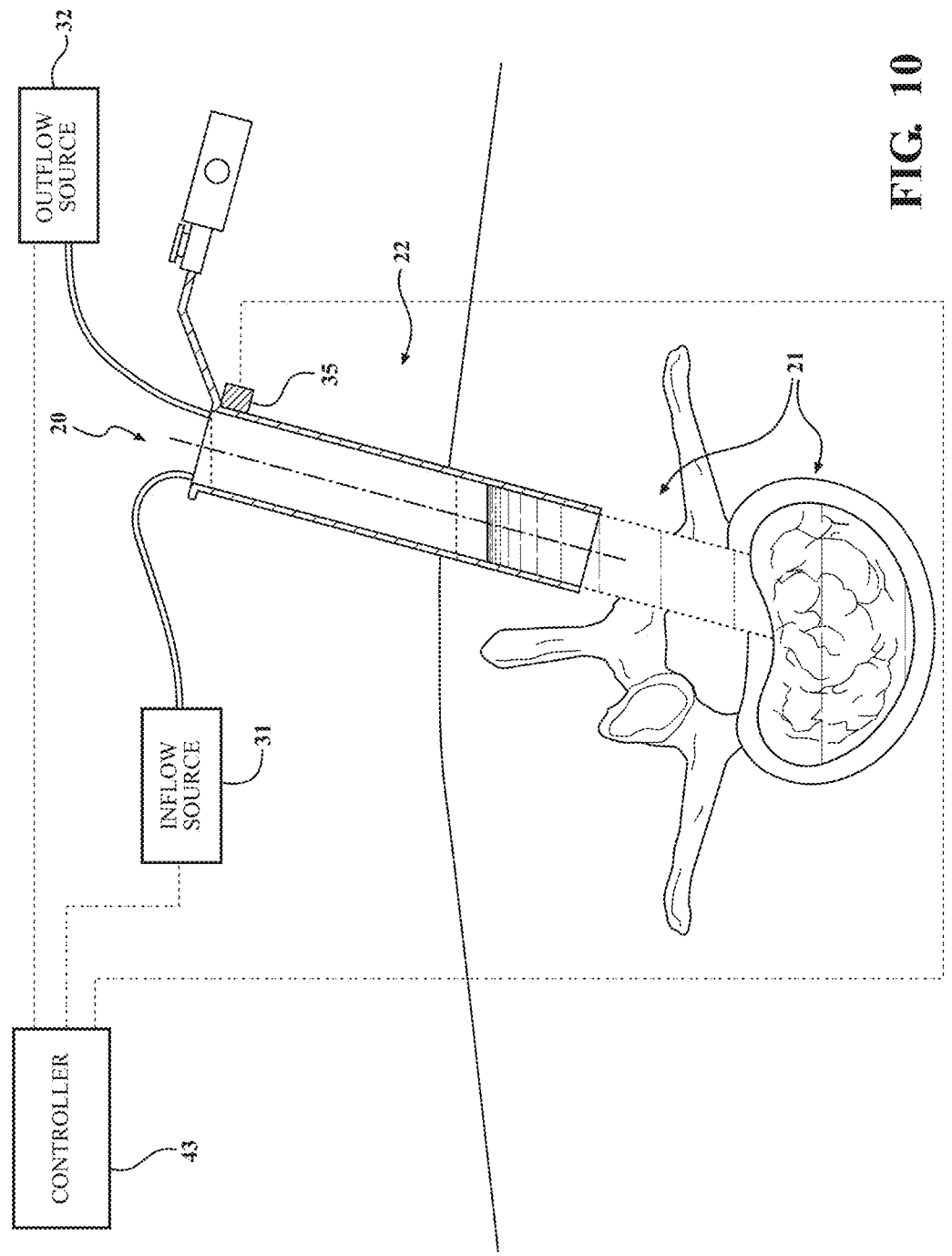
FIG. 10 is an illustration of another variation of the surgical system including a tilt sensor coupled to the retractor.

Referring now to FIG. 10, in another variation, the aforementioned retractor 22 may further include a tilt sensor 35 in communication with any of the aforementioned controller(s) and configured to generate a signal pertaining to an orientation of the retractor 22. Based on the sensed orientation of the retractor 22, the aforementioned controller(s) may control at least one of the outflow source 32 or the inflow source 31. For example, if the sensed orientation is beyond a defined deviation from upright, the controller(s) may automatically prevent operation of the surgical system 20. For example, the tilt sensor 35 may include an accelerometer, a gyroscope, or another sensor for determining orientation. Likewise, the surgical system 20 may include additional or separate accelerometer(s) or gyroscope(s) configured to detect sudden movement of the retractor 22 of the surgical system 20, which is desired to remain relatively stable during the surgical operation. If a sudden movement is detected beyond a predetermined threshold, the controller(s) may terminate operation of the surgical system 20. Still further, the surgical system 20 may include a device sensor (not shown) configured to prevent inadvertent operation of the surgical system 20 unless the device sensor is coupled to the retractor 22. In one example, the device sensor may be a clip with a readable tag (e.g., radiofrequency identification (RFID) tag) that, once coupled to the retractor 22 and detected by a complementary reader, permits operation of the surgical system 20 in the manners described throughout the present disclosure. Conversely, if the readable tag is not detected by the complementary reader, operation of the surgical system 20 is prevented.

The surgical system 20 may include a retention member 30 adapted to maintain the position of the retractor 22 relative to the patient or other desired structure within the surgical site. FIG. 2 shows the retention member 30 including a flange rigidly coupled to the retractor 22. The retention member 30 may be operably coupled to a robot, for example the MAKO® Robotic-Arm Assisted Technology (MAKO Surgical Corp., Ft. Lauderdale, Flor.) utilizing a surgical navigation system (not shown) to precisely maintain the pose (i.e., position and orientation) of the retractor 22, particularly in response to any movement of the patient.

In another variation, a deflectable valve (not shown) may be coupled to the retractor 22 and disposed within the opening 29. In one example, the deflectable valve is a duckbill valve. In one example, the deflectable valve is a diaphragm formed from material (e.g., an elastomer) adapted to be impaled by the surgical instrument(s) 62. A partial seal between the valve and the instrument(s) may be provided such that the level of fluid maintained in the retractor 22 remains at or near atmospheric pressure, yet egress of the fluid from the working channel 28 through the opening 29 is prevented. It is further contemplated that an illumination source (not shown) may be coupled to the retractor 22 and configured to provide illumination through the working channel 28.

The present disclosure also pertains to various methods of performing a surgical procedure at a surgical site 21 of a spine of a patient. In one variation shown in FIG. 11, the method includes the steps of: positioning a retractor 22 in a patient's back such that the distal end 26 of the retractor 22 is located adjacent to a surgical site 21 at the patient's spine, providing a fluid from an inflow source 31 to the surgical site 21 to form a volume of fluid 41 disposed in the surgical site 21 and the retractor 22, sensing a level of a fluid disposed in the retractor 22 using a sensor 33, and controlling the inflow source 31, an outflow source 31, or a combination thereof based on the sensed level of fluid in the retractor 22 such that fluid is maintained in the retractor 22. For example, the volume of the fluid 41 maintained in the retractor 22 may be a threshold level of fluid 48. Among other advantages, maintaining fluid in the retractor 22 may assist a surgeon with visualization of the surgical site 21 from an endoscope 66 or improve cooling of a surgical instrument 62 (not shown in FIG. 9) and the nearby tissue.

In certain variations of the various methods of the present disclosure, the method further includes a step of receiving user input to a controller 43 pertaining to the threshold level of fluid 48 to be maintained in the retractor 22 and controlling the outflow source 32 and the inflow source 31 based on the user input signal. The user input signal may be provided by a user input device (not shown), such as a button, GUI, knob, slider, etc. that provides the operator with an interface capable of providing the user input signal to the controller 43 in order to modulate operational parameters of the surgical system 20, such as the threshold level of fluid 48. For example, the user input signal may pertain to the desired level of fluid to be maintained at the surgical site 21 and within the retractor 22 during operation of the surgical system 20. Furthermore, in certain additional variations of the method of the present disclosure, the method further includes a step of receiving user input to the controller 43 pertaining to a turnover rate of fluid and controlling the outflow source 32 and the inflow source 31 based on the user input signal. The turnover rate of the fluid disposed in the retractor 22 may pertain to a synchronized inflow rate of fluid to the surgical site 21 coordinated with the outflow rate of fluid from the surgical site 21 to ensure a continuous supply of fresh fluid to the surgical site 21 to clear any debris and facilitate clear visualization, the rate of which may be adjusted up or down by the user based on situational needs.

With reference to FIG. 12, in a further variation of the methods of the present disclosure, the aforementioned step of positioning the retractor 22 may further include the steps of: positioning consecutively a K-wire (not shown), a plurality of dilators 58 sequentially increasing in diameter, and a retractor 22 having a distal end 26 and a proximal end 27 such that the plurality of dilators 58 and the distal end 26 of the retractor 22 are at a location adjacent to the surgical site 21 at the patient's spine, and removing the plurality of dilators 58 and the K-wire such that the retractor 22 remains to provide a working channel 28 to the location adjacent to the surgical site 21 at the patient's spine.

In some endoscopic procedures, such as those pertaining to the spine, the surgical site 21 cannot be subjected to substantial barometric pressure. In some instances, the surgical site 21 may not be pressurized due to physiological constraints within the region, while in other instances it may be impractical. Therefore, in another variation, the step of providing a fluid to the surgical site 21 via the inflow source 31 further includes providing the fluid to the surgical site 21 without exposing the surgical site 21 to a pressure greater than atmospheric pressure (e.g. 1 atm).

Figure 11:
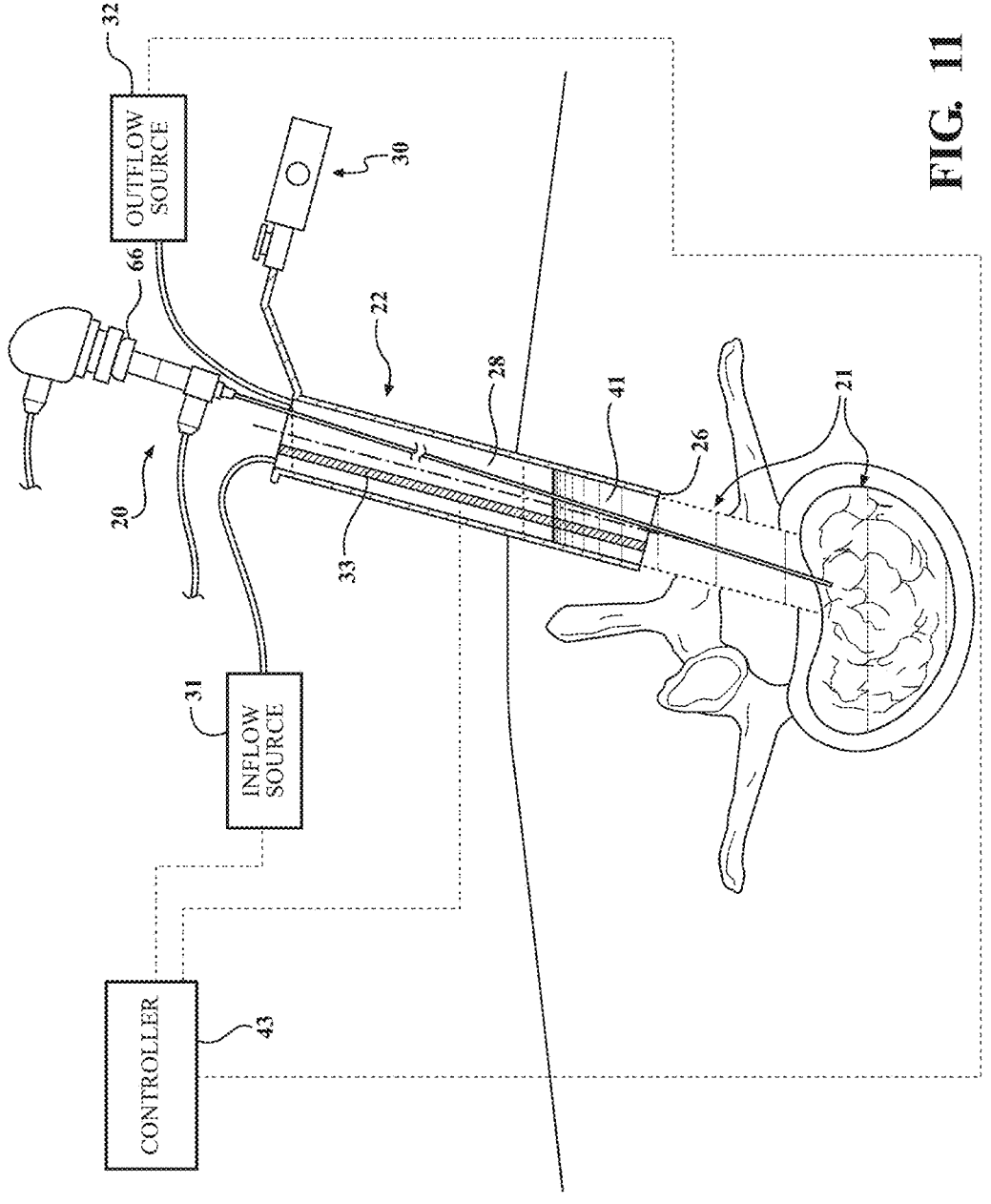
FIG. 11 is an illustration of a method of using the surgical system including a step of maintaining a level of fluid in the retractor.

Referring to FIGS. 9, 11, and 12, a distal end of the endoscope 66 may be inserted through the retractor 22 and submerged within the volume of fluid 41. One exemplary endoscope 66 suitable for the present application includes the 1188 HD 3-Chip Camera manufactured by Stryker Corporation (Kalamazoo, Mich.). It is contemplated that a camera (or an illumination source) may be coupled near a distal end of a nosetube of the surgical instrument 62 (or at or near a distal end of the outer tube of the shaver). It is further contemplated that the lens or imaging sensor may be a component of a steerable assembly, i.e., configured to articulate within the anatomy of the patient in response to an input from the user. One exemplary steerable camera suitable for the present application is disclosed in commonly owned International Publication No. WO2017/139304, filed Feb. 10, 2017, the entire contents of which are hereby incorporated by reference. Alternatively, a microscope may be used in lieu of the endoscope 66.

The endoscope 66 of FIGS. 9, 11 and 12 includes a shaft defined between the distal end and a proximal end opposite the distal end. At or near the distal end of the endoscope 66 is the lens or image sensor in communication with the camera at or near a handpiece of the endoscope 66. The proximal end of the shaft may be coupled to the handpiece adapted to be grasped and manipulated by a physician. The distal end of the shaft, and more particularly the lens or the image sensor, is submerged within the volume of fluid 41. In certain configurations, the surgical instrument 62 may be operated to rotate the cutting member 60 within the field of view of the endoscope 66 during at least a portion of the surgical procedure. With the inflow or outflow being removed from the volume of fluid 41, the fluid turnover minimizes obstruction of the field of view of the endoscope

66, further realizing the benefits of performing the tissue resection within the volume of fluid 41. For example, with the inflow or outflow being provided or removed, a swirling effect may result that moves debris away from the lens or the image sensor at the distal end of the endoscope 66.

In some variations, the method may further include the step of submerging a cutting member 60 of a surgical instrument 62 within the volume of fluid 41 and operating the surgical instrument 62 submerged within the volume of fluid 41 to resect tissue. As used herein, submerged means to be positioned within the volume of fluid 41 and/or positioned beneath the surface of the fluid. The surgical instrument 62 is operated to rotate the cutting member 60 within the volume of fluid 41 to resect tissue within the intervertebral disc space (IVDS). For surgical instruments 62 with the cutting member 60 including a bur head, the method may include submerging the entirety of the bur head. The benefits of performing the tissue resection within the volume of fluid 41 are readily realized with the nearly an entirety of the cutting member 60 and the surrounding tissue being in direct contact with the fluid, thereby maximizing heat transfer to the fluid. Potential elevation of the temperature of the cutting member 60 and the surrounding tissue is limited, which may improve cutting efficiency of the cutting member 60 and/or lessen the likelihood of surrounding tissue damage.

Another exemplary surgical instrument 62 of particular interest is a shaver. The shaver includes outer tube and a tubular drive shaft rotatably disposed within the outer tube with the cutting member 60 defined between windows within each of the outer tube and the tubular drive shaft. An outflow outlet 63 (see FIGS. 10 and 11) of the surgical instrument 62 may be in communication with the windows defining the cutting member 60. The windows are adapted to be submerged within the volume of fluid 41 with the surgical instrument 62 rotating the tubular drive shaft to resect the tissue. With the outflow outlet 63 submerged within the volume of fluid 41, the benefits of powerful suction afforded by shavers are fully realized. An exemplary shaver includes the ESSx® microdebrider system (Stryker Corporation (Kalamazoo, Mich.) and/or shavers disclosed in commonly owned U.S. Pat. Nos. 6,152,941; 6,689,146; 7,717,931; 8,475,481, each which are hereby incorporated by reference in its entirety. Other suitable surgical instruments 62 may include a router, an electrode for radiofrequency (RF) ablation, a saw or a blade configured to be received by a saw driver, a scalpel, an ultrasonic tip configured to be received by a sonopet, a curette, a rasp, a trocar sleeve, biopsy forceps, ligation devices, tissue staplers, tissue scissors, the S2 xDrive®, Sumex®, Maestro®, Saber, and Aril drill systems, manufactured by Stryker Corporation (Kalamazoo, Mich.), and/or any other endoscopic cutting device configured to be received by an endo-handpiece.

As described throughout the present disclosure, the surgical system 20 includes the surgical instrument 62 with the cutting member 60 adapted to be submerged within the volume of fluid 41 to resect tissue, for example within the intervertebral disc space (IVDS) and/or the vertebral space (VS). The aforementioned bur and shaver systems may be straight or angled. One exemplary surgical instrument 62 is disclosed in commonly owned International Publication No. WO 2016/054140, the entire contents are hereby incorporated by reference. It is further contemplated that the surgical system 20 of the present disclosure may be navigation-assisted. For example, one or more navigation markers (not shown) may be coupled to the patient in a suitable location with the navigation markers detectable by an optical camera in the surgical suite, as described in commonly owned U.S. Pat. No. 9,901,407, hereby incorporated by reference in its entirety. The navigation markers may facilitate the determination of an intraoperative position of the cutting member 60 of the surgical instrument 62 within the intervertebral disc space (IVDS). Additionally or alternatively, each of the surgical instrument 62 and the endoscope 66 may include components and features of the computer-implemented navigation systems disclosed in commonly owned U.S. Pat. No. 8,657,809 and U.S. Patent Publication Nos. 2014/ 0135617 and 2014/0243658, each of which is hereby incorporated by reference in its entirety. In addition, the retractor 22 may include one or more navigation markers.

The utilization of the surgical instrument 62, the endoscope 66, and the outflow source 32 provided by the surgical system 20 may lessen or eliminate the need to remove the surgical instrument 62 from the intervertebral disc space (IVDS) once positioned therein, a significant improvement over existing methodologies using manual rongeuers discussed previously. Among other benefits, the risk of neural damage to the ascending and/or descending nerve roots is lessened. Further, the improved visualization of the endoscope 66 during use of the surgical instrument 62 provides for more thorough, targeted removal of the nucleus pulposus (NP) and more thorough, targeted preparation of the endplates in advance of placement of the interbody spacer. Satisfactory preparation of the intervertebral disc space (IVDS) can be confirmed visually without needing to rely on rudimentary methodologies associated with manual instruments without visualization.

The present disclosure described the surgical system 20 in the context of certain steps of the transformainal lumbar interbody fusion (TLIF) and laminectomy surgical procedures. However, other spine procedures well suited to be performed within the volume of fluid 41 include, but are not limited to, lateral lumbar interbody fusion (XLIF), posterior lumbar interbody fusion (PLIF), foraminotomy, facetectomy, etc. Moreover, the aforementioned systems and methods of performing surgery within the volume of fluid 41 may be well suited for other procedures involving other orifices, cavities within the human body, and/or through openings resected through skin and/or bone of the patient during the surgical procedure. Examples include the volume of fluid being provided to the ear cavity, nasal cavity, mouth cavity, or eye cavity. Further examples include the volume of fluid being provided to a craniotomy during neurosurgery, a joint cavity during orthopedic surgery, or a soft tissue void space during cardiothoracic surgery.

Several variations of the surgical system have been discussed in the foregoing description. However, the variations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A surgical system for performing a surgical procedure at a surgical site of a spine of a patient, the surgical system comprising:

a retractor having a proximal end defining an opening to ambient, a distal end, an inner surface defining a working channel, wherein the distal end is configured to be positioned within the patient to provide the working channel to the surgical site;

an inflow source coupled to the retractor for providing a fluid to the surgical site to form a volume of fluid within the working channel of the retractor;

an outflow source for removing a volume of fluid from the surgical site, the outflow source having an outflow sensor for providing an outflow input signal;

a fluid level sensor disposed about the inner surface of the retractor such that the fluid level sensor is configured to be at least partially disposed within the patient, wherein the fluid level sensor is configured to provide a fluid level sensor input signal based on a level of the fluid disposed in the working channel; and a controller in communication with at least one chosen from the inflow source and the outflow source, and configured to control a flow rate of fluid being provided by the inflow source, an outflow rate of fluid being removed by the outflow source, or a combination thereof based on the fluid level sensor input signal and the outflow input signal.

2. The surgical system of claim 1, wherein the outflow sensor is a pressure sensor, flowrate sensor, or a combination thereof.

3. The surgical system of claim 1, wherein the fluid level sensor comprises an electrical fluid sensing member.

4. The surgical system of claim 3, wherein the electrical fluid sensing member is configured for sensing impedance or resistance.

5. The surgical system of claim 1, wherein the retractor further comprises a tilt sensor coupled to the retractor and in communication with the controller, wherein the tilt sensor is configured to sense an orientation of the retractor.

6. The surgical system of claim 1, wherein the controller is further configured to receive a user input signal corresponding to a threshold level of the fluid to be disposed within the working channel, and control the outflow source and the inflow source based on the user input signal.

7. The surgical system of claim 6, wherein the controller is configured to compare the threshold level of fluid and the fluid level sensor input signal, and, based on the comparison of the threshold level of fluid and the fluid level sensor input signal, the controller is configured to control the outflow source and the inflow source.

8. The surgical system of claim 1, wherein the controller is further configured to receive a user input signal corresponding to a turnover rate of the fluid within the working channel, and control the outflow source and the inflow source based on the user input signal.

9. A surgical system for performing a surgical procedure at a surgical site of a spine of a patient, the surgical system comprising:

a retractor having a proximal end defining an opening to ambient, a distal end, an inner surface defining a working channel, wherein the distal end is configured to be positioned within the patient to provide the working channel to the surgical site;

an inflow source coupled to the retractor for providing a fluid to the surgical site to form a volume of fluid within the working channel of the retractor, the inflow source having an inflow sensor for providing an inflow input signal;

an outflow source for removing a volume of fluid from the surgical site;

a fluid level sensor disposed about the inner surface of the retractor such that the fluid level sensor is configured to be at least partially disposed within the patient, wherein the fluid level sensor is configured to provide a fluid level sensor input signal based on a level of the fluid disposed in the working channel; and a controller in communication with at least one chosen from the inflow source and the outflow source, and configured to control a flow rate of fluid being provided by the inflow source, an outflow rate of fluid being removed by the outflow source, or a combination thereof based on the fluid level sensor input signal and the inflow input signal.

10. The surgical system of claim 9, wherein the inflow sensor is a pressure sensor, flowrate sensor, or a combination thereof.

11. The surgical system of claim 9, wherein the fluid level sensor comprises an electrical fluid sensing member.

12. The surgical system of claim 11, wherein the electrical fluid sensing member is configured for sensing impedance or resistance.

13. The surgical system of claim 9, wherein the retractor further comprises a tilt sensor coupled to the retractor and in communication with the controller, wherein the tilt sensor is configured to sense an orientation of the retractor.

14. The surgical system of claim 9, wherein the controller is further configured to receive a user input signal corresponding to a threshold level of the fluid to be disposed within the working channel, and control the outflow source and the inflow source based on the user input signal.

15. The surgical system of claim 14, wherein the controller is configured to compare the threshold level of fluid and the fluid level sensor input signal, and, based on the comparison of the threshold level of fluid and the fluid level sensor input signal, the controller is configured to control the outflow source and the inflow source.

16. The surgical system of claim 9, wherein the controller is further configured to receive a user input signal corresponding to a turnover rate of the fluid within the working channel, and control the outflow source and the inflow source based on the user input signal.

17. A surgical system for performing a surgical procedure at a surgical site of a spine of a patient, the surgical system comprising:

a retractor having a proximal end defining an opening to ambient, a distal end, an inner surface defining a working channel, wherein the distal end is configured to be positioned within the patient to provide the working channel to the surgical site;

an inflow source coupled to the retractor for providing a fluid to the surgical site to form a volume of fluid within the working channel of the retractor, the inflow source having an inflow sensor for providing an inflow input signal;

a first outflow source coupled to the retractor for removing a volume of fluid from the surgical site, the first outflow source having an outflow sensor for providing an outflow input signal;

a second outflow source configured in fluid communication with a surgical instrument having a cutting member for removing the volume of fluid from the surgical site;

a fluid level sensor disposed about the inner surface of the retractor such that the fluid level sensor is configured to be at least partially disposed within the patient, wherein the fluid level sensor is configured to provide a fluid level sensor input signal based on a level of the fluid disposed in the working channel;

a first controller in communication with the inflow source and the fluid level sensor; and a second controller in communication with the first controller and the first outflow source;

wherein the first controller is configured to control the inflow source to control a flow rate of fluid being provided by the inflow source, and the second controller is configured to control the first outflow source to control an outflow rate of fluid being removed by the first outflow source based on the sensor input signal, the inflow input signal, and the outflow input signal to compensate for sensed changes due to operation of the second outflow source such that a threshold level of fluid is maintained in the retractor.

18. The surgical system of claim 17, wherein the outflow sensor is a pressure sensor, flowrate sensor, or a combination thereof.

19. The surgical system of claim 17, wherein the inflow sensor is a pressure sensor, flowrate sensor, or a combination thereof.

20. The surgical system of claim 17, wherein the first controller is configured to receive a user input signal corresponding to the threshold level of fluid disposed in the retractor for controlling the inflow source and the first outflow source based on the user input signal.

* * * * *